(12) United States Patent
Kovac et al.

(10) Patent No.: US 8,691,151 B2
(45) Date of Patent: Apr. 8, 2014

(54) OPTO-FLUIDIC ARCHITECTURE FOR PARTICLE MANIPULATION AND SORTING

(75) Inventors: Joseph Kovac, Fort Worth, TX (US); Joel Voldman, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 476 days.

(21) Appl. No.: 12/439,650

(22) PCT Filed: Aug. 27, 2007

(86) PCT No.: PCT/US2007/018806
§ 371 (c)(1),
(2), (4) Date: Mar. 2, 2009

(87) PCT Pub. No.: WO2008/088395
PCT Pub. Date: Jul. 24, 2008

(65) Prior Publication Data
US 2009/0258383 A1    Oct. 15, 2009

Related U.S. Application Data

(60) Provisional application No. 60/841,208, filed on Aug. 31, 2006.

(51) Int. Cl.
*G01N 33/00* (2006.01)

(52) U.S. Cl.
USPC .... 422/73; 422/82.05; 422/82.09; 422/82.11; 422/502; 422/503; 422/504; 436/164; 436/177; 436/43; 436/63; 435/29; 435/4; 435/7.1; 506/30; 530/408; 714/752; 250/214.1; 250/251; 250/576

(58) Field of Classification Search
USPC .......... 422/73, 82.05, 82.09, 82.11, 502, 503, 422/504; 436/164, 177, 43, 63; 435/29, 4, 435/6, 7.1; 506/30; 250/214.1, 251, 576; 530/408; 714/752
See application file for complete search history.

(56) References Cited

U.S. PATENT DOCUMENTS

| | | | |
|---|---|---|---|
| 2002/0132315 A1* | 9/2002 | Wang et al. | 435/173.1 |
| 2004/0166555 A1* | 8/2004 | Braff et al. | 435/29 |
| 2006/0060767 A1 | 3/2006 | Wang et al. | |
| 2006/0177940 A1 | 8/2006 | Furst | |

* cited by examiner

*Primary Examiner* — Dennis M White
(74) *Attorney, Agent, or Firm* — Mark S. Cohen; Pearl Cohen Zedek Latzer Baratz LLP

(57) ABSTRACT

This invention provides an apparatus for particle sorting, particle patterning, and methods of using the same. The sorting or patterning is opto-fluidics based, in that particles are applied to individual chambers in the device, detection and/or analysis of the particles is carried out, such that a cell or population whose removal or conveyance is desired is defined, and the cell or population is removed or conveyed via application of an optical force and flow-mediated conveyance or removal of the part.

86 Claims, 13 Drawing Sheets

1  5

2  6

3  7

1-10

4

OPTO-FLUIDIC ARCHITECTURE FOR PARTICLE MANIPULATION AND SORTING

CROSS-REFERENCE TO RELATED APPLICATIONS

This application is a National Phase Application of PCT International Application No. PCT/US07/18806, International Filing Date Aug. 27, 2007, claiming priority of U.S. Provisional Patent Application 60/841,208, filed Aug. 31, 2006, all of which are incorporated herein by reference in their entirety.

GOVERNMENT INTEREST STATEMENT

This invention was made in whole or in part with government support under Grant Number RR19652, awarded by the National Institute of Health. The government may have certain rights in the invention.

BACKGROUND OF THE INVENTION

A wide array of applications exists for which the ability to specifically select desired particles, or remove undesirable particles is useful. Such applications in particular may be served by the ability to sort particles, based upon visual information.

One such application is for the sorting of particular cells in a given sample. Such application may be desirable for predicating sorts on, for example, temporal and spatial behavior of cells. To date the most conventionally used means for such application is flow-assisted cell sorting (FACS). While FACS enables high throughput sorting, such sorts are based on whole-cell fluorescence at a single timepoint. Moreover, FACS necessitates use of relatively large cell samples.

While laser capture microdissection (LCM) is another means which has been used to sort non-viable cells from microwell arrays, however its live-cell sorts require the use of proprietary films. A sorting apparatus which can be readily scaled, requiring no electrical interconnects or support electronics to address cells, allows for diverse surface functionalization, requires seconds to remove a cell of interest, and provides for simple retrieval of released viable cells is desirable and currently lacking.

SUMMARY OF THE INVENTION

In one embodiment, this invention provides a particle sorting apparatus comprising:
a particle sorter, comprising:
  a substrate comprising two or more chambers, wherein said chambers are sized to accommodate a desired number of particles;
  at least one inlet for the introduction of fluids into said sorter; and
  at least one outlet for the collection of a fluid from said sorter;
a detection system operationally connected to said sorter; and
a controllable optical force source operationally connected to said sorter applying an optical force to said particles having a beam waist about comparable to a diameter of said particle whose sorting is desired;
whereby particles in a fluid introduced into said sorter via said inlet occupy said chambers, desired particles for removal from said sorter are detected and removed via application of said optical force under flow and desired particles are conveyed to said outlet.

In one embodiment, this invention provides a method of particle sorting, said method comprising:
applying a fluid comprising particles to an inlet of a particle sorting apparatus, said apparatus comprising:
  (i) a particle sorter comprising:
    a substrate comprising two or more chambers, wherein said chambers are sized to accommodate a desired number of particles;
    at least one inlet for the introduction of fluids into said sorter; and
    at least one outlet for the collection of a fluid from said sorter;
  (ii) a detection system operationally connected to said sorter; and
  (iii) a controllable optical force source operationally connected to said sorter applying an optical force to said particles having a beam waist about comparable to a diameter of said particle whose sorting is desired;
detecting said particles and assigning at least a subset of said detected particles for removal; and
applying an optical force under flow to said particles assigned for removal whereby upon applying fluid to said device, said particles are accommodated in said chambers and application of said optical force to said subset of particles under flow conveys said subset of particles to said outlet.

In another embodiment, this invention provides a method of particle patterning on a substrate, said method comprising:
applying a fluid comprising particles to an inlet of a particle sorting apparatus, said apparatus comprising:
  a particle sorter comprising:
    a first substrate comprising two or more chambers, wherein said chambers are sized to accommodate a desired number of particles;
    at least one inlet for the introduction of fluids into said sorter; and
    at least one outlet for the conveyance of fluids out of said sorter;
  a second substrate comprising said sorter and channels linked to said outlet of said sorter;
  a detection system operationally connected to said sorter; and
  an optical force source operationally connected to said sorter;
detecting said particles and assigning at least a subset of said detected particles for conveyance from said sorter to at least a portion of said channels; and
applying an optical force under flow to said particles assigned for conveyance
whereby said optical force applied under flow conveys said particles to said channels and cessation of said optical force and said applied flow allows for patterning of said particles on said second substrate.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
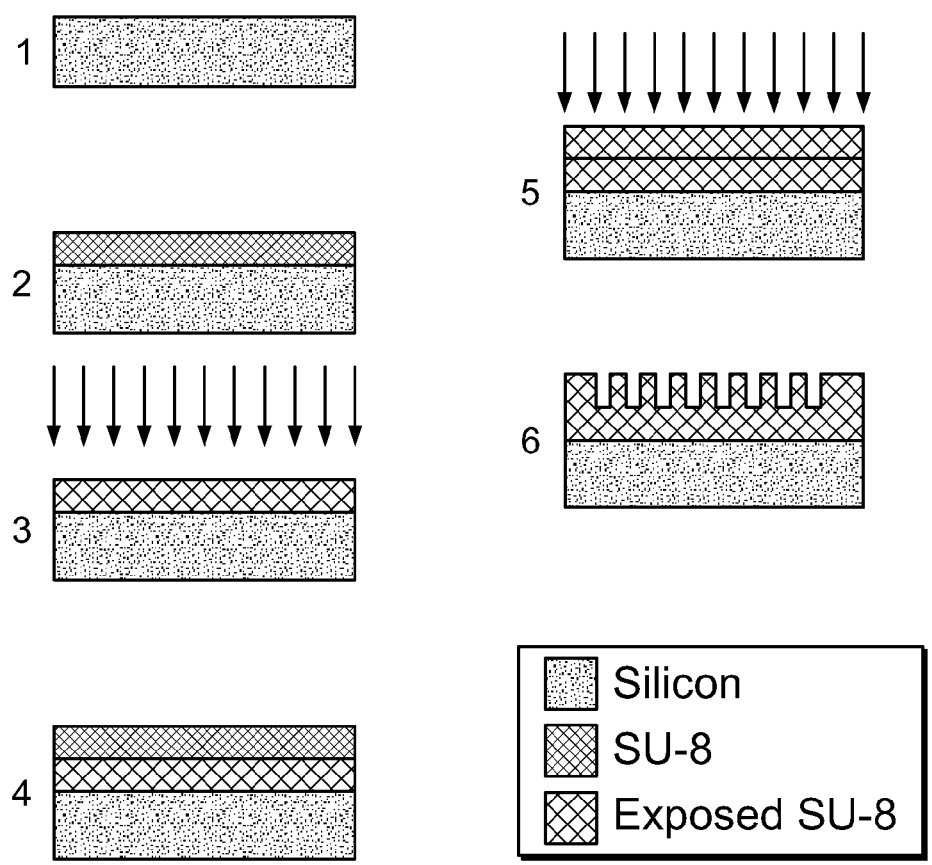
FIG. 1A schematically depicts a cross section of the process for preparing one embodiment of the device. The flow diagram depicts the various stages for preparing the array. (1) Starting substrate is a test-grade silicon wafer. (2) SU-8 spin-on and prebake. (3) expose mask 1, post-bake. (4) SU-8 spin-on and prebake. (5) Expose mask 2, post-bake. (6) Develop.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, inter-alia, devices, apparatuses and methods of particle sorting or particle patterning. In one embodiment, particle sorting or patterning is based upon visual information, and may be referred to herein as "opto-fluidic particle or cell sorting" (OPTO-FluPS or OPTO-FluCS, respectively).

OPTO-FluPS or OPTO-FluCS is opto-fluidics based, in that particles are applied to individual chambers in the device or apparatus, and detection and/or analysis and/or selection of the particles is carried out, such that a particle whose removal or conveyance is desired is defined, and the particles is removed or conveyed via application of an optical force and flow-mediated conveyance or removal of the particle.

In one embodiment, this invention provides a particle sorting apparatus comprising:
  a) a particle sorter, comprising:
    a substrate comprising two or more chambers, wherein said chambers are sized to accommodate a desired number of particles;
    at least one inlet for the introduction of fluids into said sorter; and
    at least one outlet for the collection of a fluid from said sorter;
  b) a detection system operationally connected to said sorter; and
  c) an optical force source operationally connected to said sorter;

whereby particles are introduced into said sorter via said inlet and occupy said chambers, desired particles for removal from said sorter are detected and removed via application of said optical force under flow to said desired particles in said chambers which conveys said particles to said outlet.

In one embodiment, this invention provides a particle sorting apparatus comprising:

a) a particle sorter, comprising:

a substrate comprising two or more chambers, wherein said chambers are sized to accommodate a desired number of particles;

at least one inlet for the introduction of fluids into said sorter; and at least one outlet for the collection of a fluid from said sorter;

b) a detection system operationally connected to said sorter; and c) a controllable optical force source operationally connected to said sorter applying an optical force to said particles having a beam waist about comparable to a diameter of said particle whose sorting is desired;

whereby particles in a fluid introduced into said sorter via said inlet occupy said chambers, desired particles for removal from said sorter are detected and removed via application of said optical force under flow and desired particles are conveyed to said outlet.

In one embodiment, the term "particle" or "particles" refers to a material which is insoluble in the fluid in which it is dispersed. In one embodiment, the particles are in a liquid, or in another in a gas. In one embodiment, the particles comprise a pure substance such as salt, metal, nonmetal inorganic atomic material, nonmetal inorganic molecular material, organic compound or in another embodiment, a homogeneous or a heterogeneous mixture of any combination thereof. In another embodiment, the particles are heterogeneous solid materials. In some embodiments, the particles are cells, or organelles or combinations thereof. In some embodiments, the particles are homogenates of cells. In some embodiments, the particles are subcellular fractions. In some embodiments, the particles are any biomolecule, for example, proteins, peptides, nucleic acids, glycoproteins, carbohydrates, lipids, or combinations thereof. In some embodiments, the cells are eukaryotic, and in some embodiments, are suspended in a fluid medium.

The apparatuses of this invention comprise particle sorters. The term "apparatus", in some embodiments, is to be considered interchangeable with that of "device" either of which is to be understood as comprising the elements as described herein.

The particle sorters of this invention comprise at least one substrate which in turn comprises chambers. In one embodiment, the term "chamber" or "well" are interchangeable and refer to a structure which is suitable for the housing or at least partial enclosure of a particle, as herein described. The dimensions of such wells or chambers, in turn, will reflect the particular application for use, for example, the size of individual particles, or number of particles or shape or volume of particles, of which sorting or patterning is desired, as described herein.

In some embodiments, such chambers or wells are raised with respect to the substrate plane, and are adhered to the substrate via any conventional means, for example via the use of a gasket, or adhesive, or deposition of the material. In some embodiments, such chambers or wells are recessed with respect to the plane of the substrate. In some embodiments, the material comprising the substrate is the same as that comprising the chambers, such that they are contiguous.

In one embodiment, the wells are shaped and sized to hold individual cells such as adherent cells, neoplastic cells, preneoplastic cells, neuronal cells, microglia cells, giant cells, hormone secreting cells, metabolism and storage cells, barrier function cells, ECM secreting cells, contractile cells, blood and immune system cell, germ cells, stem cells, fused cells, primary cells, cell lines, bacterial cells, yeast, protests, or any desired cell which can be contained within the device.

In some embodiments, the substrate further comprises microfluidic or nanofluidic channels. In some embodiments such channels will be configured as to be adjacent to the chambers or wells of the sorter. In some embodiments such channels are positioned proximally to the chambers, such that upon application of the optical force as described herein, the force may convey the particles from the chambers to the microchannels. In some embodiments, the channels are positioned proximally to an outlet, as well, such that particles are conveyed via the channels to an outlet. In some embodiments, such channels will be present in roughly similar vertical planar positions, with respect to the opening of the wells or chambers of the sorters. In some embodiments, such channels will be raised with respect to the opening of the wells or chambers, or in some embodiments recessed. In some embodiments, the sorters of this invention will comprise channels positioned at various heights with respect to the opening of the wells or chambers in the sorters. In some embodiments, the apparatus further comprises a collection module operationally positioned proximally to the outlet, such that sorted/selected particles are conveyed via the outlet to the collection module.

It is to be understood that the terms "sort" "sorting" or "sorted" refer, in some embodiments, to any selection means where particular particles or populations of particles are chosen for conveyance or removal from the sorter device. In some embodiments, the terms refer to particles which remain within the chambers of the device, whose removal was not desired, thus were selected to remain within the chambers which they occupy.

In some embodiments, the channel depth, width, or combination thereof, will vary in the sorters of this invention. In some embodiments, the design of these parameters of the channels in the sorters of this invention will be a reflection of the material to be conveyed, the distance conveyed, the flow rate or pressure applied, or a combination thereof.

In some embodiments, the sorter is a chip, comprising the wells or chambers, and optionally the channels as herein described. In some embodiments, the chambers and/or channels in the devices of this invention will have dimensions on the order of microns, or in some embodiments, on the order of millimeters, or in some embodiments, on the order of nanometers, or in some embodiments, on the order of centimeters, to suit a desired application. In some embodiments, chamber size may vary within a given device and such size variance may be over a range of several orders of magnitude, or more, to suit a desired application. Similarly, in some embodiments, the channel size may vary within a given device, etc.

In some embodiments, the width of the chamber ranges from 5-1000 μm, the length of the chamber ranges from 500 μm-8 mm, and the depth of the chamber ranges from 1 μm-10 mm. In some embodiments, the width of the channels range from 5-1000 μm, and the depth of the channels range from 1 μm-10 mm. In some embodiments, the channels will have dimensions which roughly correspond to that of the chamber, though the length will exceed that of the chambers by several orders of magnitude. In some embodiments, the dimensions of the channels may be incrementally smaller, as a function of their distance from the chambers.

In some embodiments, the composition of the substrate will depend on a variety of factors, including the techniques used to create the device, the use of the device, the composition of the sample, the particles to be sorted, the type of analysis conducted prior to, and/or following sorting, the size of internal structures, the presence or absence of additional components on the sorter, and the technique used to move fluid, etc. In some embodiments, the sorters of the invention should be easily sterilizable, although in some applications this is not required. In some embodiments, the sorting devices are disposable or re-usable.

In one embodiment, the substrate can be made from a wide variety of materials including, but not limited to, silicon, silicon dioxide, silicon nitride, glass and fused silica, gallium arsenide, indium phosphide, III-V materials, PDMS, PEG, photo patterned PEGDA, silicone rubber, aluminum, ceramics, polyimide, quartz, plastics, resins and polymers including polymethylmethacrylate, acrylics, polyethylene, polyethylene terephthalate, polycarbonate, polystyrene and other styrene copolymers, polypropylene, polytetrafluoroethylene, superalloys, zircaloy, steel, gold, silver, copper, tungsten, molybdenum, tantalum, KOVAR, KEVLAR, KAPTON, MYLAR, teflon, brass, sapphire, etc. High quality glasses such as high melting borosilicate or fused silicas may be used, in some embodiments, for example, for their light transmission properties when any of the sample manipulation and/or detection steps require light based technologies. In addition, as outlined herein, portions of the internal and/or external surfaces of the device may be coated with a variety of coatings as needed, to facilitate, in some embodiments, the manipulation or detection technique performed.

Assembly of such configurations is well known to the skilled artisan, and an embodiment of such construction is provided herein below in Example 1.

In some embodiments, fabrication of the sorters of the invention, may be via a variety of techniques, including, but not limited to, hot embossing, such as described in H. Becker, et al., Sensors and Materials, 11, 297, (1999), hereby incorporated by reference, molding of elastomers, such as described in D. C. Duffy, et. al., Anal. Chem., 70, 4974, (1998), hereby incorporated by reference, injection molding, LIGA, soft lithography, silicon fabrication and related thin film processing techniques, as known in the art. In one embodiment, glass etching and diffusion bonding of fused silica substrates may be used to prepare the sorters of this invention.

According to this aspect of the invention and in one embodiment, the apparatus comprises a non-conductive material, such as glass or PDMS, or in another embodiment, a conductive or semi-conductive material. In another embodiment, the sorters comprise at least one exposed surface which is transparent.

The sorters of this invention will comprise at least one inlet and at least one outlet, for the application and removal, respectively of fluids to and from the sorter. In some embodiments, multiple inlets, outlets, or combinations thereof are present in the sorters. In some embodiments, multiple fluids are introduced or removed, respectively, from a single, a few, or individual inlets and outlets, respectively.

In one embodiment, at least one of the inlets of the apparatus serves for the introduction of a buffered solution comprising particles whose sorting is desired. In another embodiment, a second inlet serves for the introduction of a second buffer, which may for example, comprise a reagent for the assay or visualization of the particles. The skilled artisan will appreciate that the fluids which are introduced to the sorter may serve an unlimited number of purposes, which are desirable when sorting or patterning particles using the devices and/or according to the methods of this invention, and any such introduction represents an embodiment thereof.

In another embodiment, the fluids for use according to the methods and for use in the devices of this invention may comprise any fluid that will suit a desired purpose. For introduction of the particles to the sorter, the fluid will comprise particles for separation, or patterning, and may include for example, bodily fluids such as, in some embodiments, blood, urine, serum, lymph, saliva, anal and vaginal secretions, perspiration and semen, or in another embodiment, homogenates of solid tissues, as described, such as, for example, liver, spleen, bone marrow, lung, muscle, nervous system tissue, etc., and may be obtained from virtually any organism, including, for example mammals, rodents, bacteria, etc. In some embodiments, the sorter separates mixed components into individual structures, e.g., different cells are sorted into individual chambers of the device.

In some embodiments, the solutions or buffered media may comprise environmental samples such as, for example, materials obtained from air, agricultural, water or soil sources, which are present in a fluid which can be subjected to the methods of this invention. In another embodiment, such samples may be biological warfare agent samples; research samples and may comprise, for example, glycoproteins, biotoxins, purified proteins, etc.

The devices of this invention in addition to the sorters further comprise a detection system operationally connected to the sorter. The term "detection system" in this context, refers to the ability to select a population of particles, which once applied to the sorter, can be distinguished as to whether the particles will be assigned for removal or conveyance from the sorter. Such "detection" may be by the naked eye of the observer, or may be via the use of any equipment or machinery which provides readout for a desired phenotype on which the selection is to be carried out. For example, in some embodiments, detection refers to machinery which detects a particular event on which the sort is based. For example, such machinery may comprise a luminometer, and the presence of luminescent particles serves as the signal for sorting such particles, or alternatively, sorting non-luminescent particles. In another embodiment such sorting may rely on the presence of fluorescence, the localization of fluorescence, the change in fluorescence as a function of time, the temporal regulation of fluorescence over a specified region, etc., as will be appreciated by one skilled in the art.

In other embodiments, detection may occur following assay of the sorted particles. For example, detection may rely on the evolution of a particular compound from assayed particles, such as, for example, the evolution of a gas within a chamber, following assay of the particle in the chamber, wherein such gas evolution may be detected, for example, by view of "bubbling" by the naked eye, or upon magnification of the particular chamber, or the accumulation of condensation over a particular region, etc.

It is to be understood that any means of selection of a subset of particles in a chamber or multiple chambers of the sorters of this invention, is to be considered as part of this invention and is to be understood as encompassed by the use of the term "detection" in reference to the devices and/or methods of this invention.

In another embodiment, detection may comprise imaging of the chamber, which may be accomplished via any means known in the art, and may include reflectance mode, or fluorescence microscopy. Imaging may be accomplished over a course of time, and in one embodiment, particles for separation may be labeled with a detectable marker, for example a fluorescent marker. In one embodiment, anti-quenching agents may be added to the solutions used according to the methods and in the devices of this invention.

For example, in some embodiments, reagents may be incorporated in the buffers used in the methods and devices of this invention, to enable chemiluminescence detection. In some embodiments the method of detecting the labeled material includes, but is not limited to, optical absorbance, refractive index, fluorescence, phosphorescence, chemiluminescence, electrochemiluminescence, electrochemical detection, voltometry or conductivity. In some embodiments, detection occurs using laser-induced fluorescence, as is known in the art.

In some embodiments, the labels may include, but are not limited to, fluorescent lanthanide complexes, including those of Europium and Terbium, fluorescein, fluorescamine, rhodamine, tetramethylrhodamine, eosin, erythrosine, coumarin, methyl-coumarins, pyrene, Malacite green, stilbene, Lucifer Yellow, Cascade Blue™, Texas Red, 1,1'-[1,3-propanediylbis[(dimethylimino-3,1-propanediyl]]bis[4-[(3-methyl-2(3H)-benzoxazolylidene)methyl]]-, tetraiodide, which is sold under the name YOYO-1, Cy and Alexa dyes, and others described in the 9th Edition of the Molecular Probes Handbook by Richard P. Haugland, hereby expressly incorporated by reference. Labels may be added to 'label' the desired molecule, prior to introduction into the sorter, in some embodiments, and in some embodiments the label is added after particle loading in the sorter. In some embodiments, the labels are attached covalently as is known in the art, or in other embodiments, via non-covalent attachment. In some embodiments, photodiodes, confocal microscopes, CCD cameras, or photomultiplier tubes maybe used to image the labels thus incorporated, and may, in some embodiments, comprise the apparatus of the invention, representing, in some embodiments, a "lab on a chip" mechanism.

Embodiments of such a scenario are exemplified herein in Example 1, which is a non-limiting example of one type of setup of such a device which, in turn, was used to sort cells based on particular marker incorporation (e.g., orange versus green, or nuclear versus membrane, see for example FIGS. 3-6).

In one embodiment, detection is accomplished using laser-induced fluorescence, as known in the art. In some embodiments, the apparatus may further comprise a light source, detector, and other optical components to direct light onto the sorter and thereby collect fluorescent radiation thus emitted. The light source may comprise a laser light source, such as, in some embodiments, a laser diode, or in other embodiments, a violet or a red laser diode. In other embodiments, VCSELs, VECSELs, or diode-pumped solid state lasers may be similarly used. In some embodiments, a Brewster's angle laser induced fluorescence detector may used. In some embodiments, one or more beam steering mirrors may be used to direct the beam to a desired location for detection.

In one embodiment, the sorter may be constructed of a material which renders it transparent or semitransparent, in order to image the solutions being sorted, or in another embodiment, to ascertain the progress of the sorting, or in another embodiment, to facilitate sorting of particles as a function of a dynamic process, etc.

In some embodiments, the materials further have low conductivity and high chemical resistance to buffer solutions and/or mild organics. In other embodiments, the material is of a machinable or moldable polymeric material, and may comprise insulators, ceramics, metals or insulator-coated metals.

In other embodiments, the sorter may be constructed from a polymer material that is resistant to alkaline aqueous solutions and mild organics. In another embodiment, the sorter comprises at least one surface which is transparent or semitransparent, such that, in one embodiment, imaging of the chamber is possible.

The device comprises inlets and outlets for the introduction of fluids, for the conveyance of selected particles, in some embodiments. In some embodiments, such inlets may in turn be in fluid communication with the chambers and/or channels in the sorters. In other embodiments, the chambers and channels are in fluid communication, and the chambers alone are in fluid communication with the inlets.

In one embodiment, inlet may comprise an area of the substrate in fluidic communication with one or more channels or chambers, or in other embodiments, in fluidic communication with one or more channels yet not in communication with the chambers.

Inlets and outlets may be fabricated in a wide variety of ways, depending on the substrate material of the sorter and the dimensions used.

In one embodiment inlets and/or outlets are formed using conventional tubing, which prevents sample leakage, when fluid is applied to the device, under pressure. In one embodiment, the inlet may further comprise a means of applying a constant pressure, to generate pressure-driven flow in the device.

In one embodiment, the buffered solution is flowed through the chamber at a relatively constant flow rate, which in one embodiment ranges from about 0.5-15 µl/minute. According to this aspect of the invention, pressure applied to the device will be such as to accommodate a relatively constant flow rate, as desired, as will be understood by one skilled in the art. According to this aspect of the invention, and in other embodiments, care will be taken to ensure unacceptable shear stresses are not applied to particles whose characteristics may change as a function of such application, for example cells and stress responses. In some embodiments, such flow rate will be a function of cell size, shape, function or a combination thereof.

In one embodiment, any of various mechanisms may be employed to manipulate, transport, and/or move fluid within the device, and/or to convey the particles within the device. In some embodiments, pressurized fluid flow is applied from a syringe, or, in another embodiment, other pressure source, attached to, in one embodiment, an inlet of a device of this invention.

In some embodiment, a pressure stop is positioned between two or more chambers in an apparatus of this invention, such that the pressure-driven flow through a first chamber does not influence the flow through a second chamber, in some embodiments of this invention.

Inlets/outlets allow access to the chambers to which they are connected for the purpose, in one embodiment, of introducing or, in another embodiment, of removing fluids from the chambers on the microfluidic chip. In one embodiment, inlets allow access to the chamber to which they are connected for the purpose of introducing fluids to the chamber, for example, from a sample reservoir, or in another embodiment, from a sample stored in a conventional storage means, such as a tube. In another embodiment, the outlet allows access of fluid comprising particles from the chamber which has undergone sorting, according to the methods of this invention. According to this aspect of the invention, the outlet may allow for the removal and storage of the sorted material, or in another embodiment, its conveyance to an analytical module, which in one embodiment, may be coupled thereto.

In one embodiment, cells, particles or other materials are applied to the devices of this invention by any means known in the art. For example, cells, particles or other materials may be delivered by directly pipetting them onto the surface of the device either manually or by robotic liquid handling systems. In some embodiments, application is via bulk delivering the cells, particles or other materials in fluid to the surface of the device and removing excess fluid by pipetting, or in some embodiments, via the application of a vacuum, or in some embodiments via the use of a physical implement to remove the cells, such as, for example, a cell scraper or rubber policeman. In some embodiments, the cells, particles or other materials are applied via the use of a delivery device with microfluidic channels to deliver the cells to the surface of the device.

In one embodiment, the substrates, chambers, channels, or a combination thereof are coated with at least one material, which minimizes particle adhesion thereto.

As referred to herein, the phrase "a" or "an", when in reference to any element or any embodiment of this invention, is to be understood as encompassing at least one of the indicated element. In some embodiments, the terms are to be taken to refer to two or more, multiples of ten, of numbers of elements which may vary by several orders of magnitude, as appropriate to the reference element.

In one embodiment the material, which minimizes particle adhesion is polytetrafluoroethylene (TEFLON), or in another embodiments, is a protein solution, which in one embodiment, comprises Bovine Serum Albumin (BSA). In some embodiments, the substrate is formed of a material which itself minimizes such adhesion, or in another embodiment the substrate may be treated to achieve this result, for example, via coating with a compound which facilitates the desired result.

In one embodiment, substrates, chambers, channels, or a combination thereof may be coated, by microstamping molecules such as polyethylene glycol (PEG) or octadecyltrichlorosilane (OTS), both of which resist protein adhesion and thereby prevent cell adhesion.

In one embodiment, the substrates, chambers, channels, or a combination thereof comprise at least one material, which promotes or stimulates adherence to the device. In some embodiments, suitable adherence promoting materials may include, but are not limited to, various carbon coatings, nitrides, metal coatings, metal alloys, biological polymers, glasses, oxides, phosphates and carbides or combinations thereof. In another embodiment, additional materials can be used for coating the substrate to promote adherence, such as, for example, coating or application of cytokines, chemokines, matrix proteins, adhesion molecules, lectins, immunoglobulins, RGD peptides (R: arginine; G: glycine; D: aspartic acid) and others, as will be appreciated by one skilled in the art.

In another embodiment, the adherence promoting materials may include, but are not limited to, an antigen, hapten, enzyme, an enzyme cofactor, a receptor agonist, a carbohydrate, a receptor, and others. In some embodiments, the presence of such molecules, alter cellular dynamics and may serve as a basis for the sorting of particles contained therein, representing an embodiment of this invention.

In another embodiment, the adherence promoting materials may include, but are not limited to, an antibody specific for various or specific mammalian cells. For example, anti-Ig kappa light chain antibody, anti-CD45R antibody, or anti-syndecan, may be used to differentially bind B-cells. Antibodies to cytokeratins may differentially bind epithelial cells, etc. Any of the methods known in the art for conjugating an antibody to a solid phase support, can be used in the present invention.

It is to be understood that any material which either promotes, stimulates, minimizes or abrogates adhesion to the devices of this invention may be implemented, and/or its effect on cellular behavior may in turn provide a basis for the sorting and/or patterning methods of this invention, and represents an embodiment thereof.

In one embodiment, the devices of this invention may comprise an integrated temperature control system. In one embodiment, on-chip temperature sensing may be conducted, and in another embodiment, may use a microscale calibration technique that gives spatial information.

In one embodiment, the temperature control system may consist of an on-chip metal temperature-sensing resistor (fabricated at the same time as the trap electrodes) and a resistively heated transparent conductive heater connected to a computer. The computer implements in software a PID (proportional-integral-differential) controller that in turn controls a heater power supply. The transparent heater may be made, in one embodiment, of indium tin oxide (ITO), a transparent conductor that is commonly used as an electrode in LCD displays and is used as a heater in a commercial environmental chamber for microscopy (Bioptechs, Inc.). In one embodiment, it is possible to place the heater anywhere in the system. In one embodiment, commercially obtained ITO-coated coverslips are used, and the solution is heated directly In one embodiment, the performance of the temperature control system can be evaluated using encapsulated thermochromic liquid crystals (TLCs) [Chaudhari, A. M., Woudenberg, T. M., Albin, M. & Goodson, K. E. Transient liquid crystal thermometry of microfabricated PCR vessel arrays. Journal of Microelectromechanical Systems 7, 345-355 (1998)]. These crystals, which are the same active ingredient found in flexible strip thermometers that patients can apply to their foreheads, change color in response to temperature differences and are readily available in formulations with responses centered around physiological temperatures and in particle sizes of several microns, giving adequate spatial resolution. They allow for the spatial integration of the image and the temperature distribution of the chip and through calibration, achieving, in one embodiment, ~0.1° C. accuracy and precision.

In another embodiment, pH is controlled in DMEM-based media via a bicarbonate buffering system. In one embodiment, pre-equilibrated media is delivered to the chip, for example via introduction to an inlet via use of gas-permeable tubing. In another embodiment, pH may be measured before and after the chip using a commercial inline microvolume pH sensor. One may, in another embodiment, image the chambers and use the phenol red indicator in DMEM to determine whether there is noticeable pH change in the medium under these conditions. If so, in another embodiment, one can adjust the $CO_2$ flowrate, etc.

In another embodiment, $O_2$ will be monitored and controlled in the same way as $CO_2$, using inline microvolume sensing and control as described herein.

In one embodiment, the devices of this invention will comprise at least one environmental controller. In some embodiments, the devices may comprise 2 or more such controllers, or in another embodiment, measures are taken to preserve desired environmental conditions.

In another embodiment, the device is constructed modularly, such that once loaded, the device containing particles may be removed, placed in an appropriately controlled environment for a prescribed period of time, and reinserted to the apparatus, for subsequent sorting.

In another embodiment, automatic fluid control may simplify operation of the device and enable precise timing of reagent additions. The external flow system may, for example, consist of 360-mm OD tubing commonly used in HPLC coupled to computer-controlled switching and injection valves and syringe pump. One may, in one embodiment, select the inner diameter of the flow paths to minimize internal volume while, for example, preventing undue shear on the cells.

The devices of this invention in addition to the sorters further comprise a detection system operationally connected to the sorter and an optical force source operationally connected to the sorter.

As is exemplified and described herein, the devices and/or methods of this invention provide for specific conveyance of a sorted particle or particle population. Such sorted particle/s can be conveyed to other regions on a substrate, and in some embodiments, can be therein deposited, which in some embodiments, may reflect a means of particle patterning. In other embodiments, such sorted particle/s can be conveyed out of the sorting device and removed for other applications, including discarding or further assay or other manipulation or storage of the sorted particle/s.

Any number of applications may be served by the ability to specifically sort a subpopulation of particles applied to a sorting device of this invention. In some embodiments, multiple sorts can be effected from the same application of the starting fluid, and is part of this invention, as well. It is to be understood that there is no limitation to the use of the particles which are sorted according to the methods and/or using the devices of this invention, which all comprise a part of this invention.

For example, and in some embodiments, the methods and apparatuses of this invention may be employed to sort and thereby determine changing size characteristics in a cell population, or in another embodiment, contamination of a medium, or in another embodiment, differentiation of cells, or in another embodiment, cell signaling events, or in another embodiment, cell growth, or in another embodiment, cell cycle arrest, or in another embodiment, differential gene expression in a cell, including in bacterial cells transformed with a library of expression vectors. In some embodiments, the methods and apparatuses of this invention may be employed to sort and thereby assess or assay subcellular localization of a particular compound, or organism, or temporal regulation of expression, or temporal regulation of vesicular traffic, or marker expression in a dynamic way for any intracellular event, or other monitoring of intracellular events, as will be appreciated by one skilled in the art. Similarly, the chambers of this invention can be so constructed to accommodate 2 or more cells per chamber in a desired proximity, such that events upon cell-to-cell contact, early events in infection, quorum sensing, etc., can be assessed, and cells/particles with desired characteristics can be sorted or patterned, for example, for further study or assay.

It is to be understood that the methods and/or apparatuses of this invention may be used for the sorting of any particle from a population of particles, or patterning of a particle present in a mixture in a fluid, representing embodiments of this invention.

The apparatus and methods of the instant inventions utilize, at least in part, forces on particles caused by light, which in turn may be applied to move a particle in a given orientation or direction. In some embodiments, by moving the light relative to the particles, typically through a medium having some degree of viscosity, particles may thus be separated based at least in part upon the optical force asserted against the particle. In some embodiments, the optical force is applied in a pattern which moves relative to the device/particle/chamber to which it is applied, however, it will be appreciated that the relative motion may be achieved otherwise, such as by maintaining the optical force source stationary and moving the subject particle, etc., relative to the source.

Any source of an optical force may be used in the devices and/or methods of this invention. In one embodiment, the source is a laser, which in one embodiment, is at biologically-compatible is infrared wavelengths, allowing precise cell characterization and manipulation with little or no effect on the cell itself.

In one embodiment, this invention provides a method of particle sorting, said method comprising:
(a) applying a fluid comprising particles to an inlet of a particle sorting apparatus, said apparatus comprising:
(i) a particle sorter comprising:
a substrate comprising two or more chambers, wherein said chambers are sized to accommodate a desired number of particles;
at least one inlet for the introduction of fluids into said sorter; and
at least one outlet for the collection of a fluid from said sorter;
(ii) a detection system operationally connected to said sorter; and
(iii) a controllable optical force source operationally connected to said sorter applying an optical force to said particles having a beam waist about comparable to a diameter of said particle whose sorting is desired;
detecting said particles and assigning at least a subset of said detected particles for removal; and
applying an optical force under flow to said particles assigned for removal
whereby upon applying fluid to said device, said particles are accommodated in said chambers and application of said optical force to said subset of particles under flow conveys said subset of particles to said outlet.

In one embodiment, this invention provides a method of particle sorting, said method comprising:
(a) applying a fluid comprising particles to an inlet of a particle sorting apparatus, said apparatus comprising:
(i) a particle sorter comprising:
a substrate comprising two or more chambers, wherein said chambers are sized to accommodate a desired number of particles;
at least one inlet for the introduction of fluids into said sorter; and
at least one outlet for the collection of a fluid from said sorter;
(ii) a detection system operationally connected to said sorter; and
(iii) an optical force source operationally connected to said sorter;
whereby said particles are accommodated in said chambers;
(b) detecting said particles and assigning at least a subset of said detected particles for removal; and
applying an optical force under flow to said particles assigned for removal whereby said optical force applied under flow conveys said particles to said outlet.

It is to be understood that any embodiment for any element described in the devices of this invention is to be considered applicable for use according to the methods of this invention, and an embodiment thereof.

For example, and in some embodiments, the particles are sorted as a function of expression, presence, or localization of said detectable marker or a combination thereof. In some embodiments, sorting, or in other embodiments, patterning of the particles according to the methods of this invention is desirable upon detection of a particular event in a dynamic series of events that occurs in the system employed, and such sorting or patterning can be effected on time scales as short as fractions of a second, or following observations for minutes, or hours, days or week, or years, as will be appreciated by one skilled in the art.

In one embodiment, the methods make use of particles tagged or conjugated to a detectable marker, which is a fluorescent molecule, or in another embodiment, is an electron dense or light reflective molecule. According to this aspect of the invention, use of such markers is particularly suited to detection via microscopy, including phase-contrast, fluorescence, confocal or atomic force microscopy.

Figure 3:
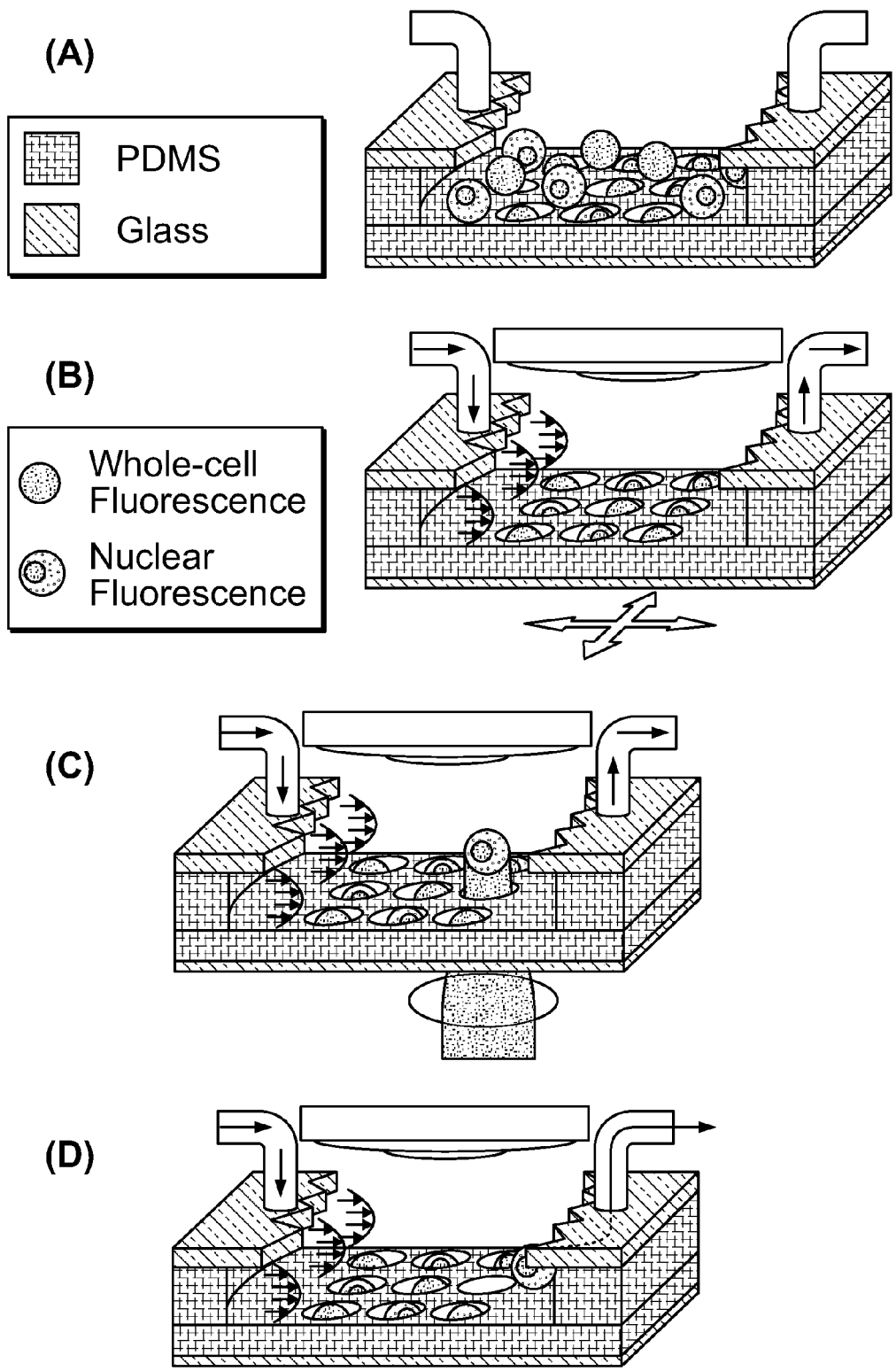
FIG. 3 schematically depicts an embodiment of the operation of an apparatus of this invention. (A) Following injection into the device, cells sediment into the microwell array. (B) Cells remaining outside wells flow away after flow resumes. The array is inspected using any desired microscopy technique (brightfield, DIC, fluorescence, etc.). (C) After locating cells of interest, an infrared (IR) laser beam is focused onto target cells, levitating the cells into the flow field with the optical scattering force. (D) Fluid drag overcomes lateral optical forces, releasing the cell and washing it downstream for further applications, e.g. fractionation.

In some embodiments, the methods of this invention employ a controller for fluid flow rate and pressure through the sorting/patterning device. In some embodiments, the optical force is applied prior to the application of flow, at which application the particle is levitated above the chamber's uppermost boundary, or close to the chamber's aperture, such that upon the application of a relatively constant flow rate and pressure, the particle is then conveyed in the direction of flow. Such a scenario is schematically depicted herein, for example, in FIG. 3, representing one embodiment of the invention.

In another embodiment, the apparatus further comprises at least one environmental controller to regulate pH or temperature in said sorter. In another embodiment, the sorter further comprises microchannels positioned proximally to the chambers, such that the applied optical force conveys particles from said chambers to said microchannels, upon application of flow. In another embodiment, the microchannels are positioned proximally to the outlet, such that the particles are conveyed via the microchannels to the outlet.

In some embodiments, the microchip comprises the sorter of the device of this invention, and in some embodiments, may comprise the channels, and additional regions for conveyance of the particle, and/or patterning the conveyed particles on other regions of the substrate, as described herein.

In some embodiments, the apparatus further comprises a collection module operationally positioned proximally to said outlet, such that said particles are conveyed via said outlet to said collection module. In some embodiments, the collection module comprises reagents for the assay of sorted particles. In some embodiments, the collection module further comprises an apparatus for the detection and analysis of the results of said assay In one embodiment, subsequent to separation via the methods and utilizing the devices of this invention, further analysis of the sorted materials is possible. Such analysis may be via direct coupling of the machinery necessary for such analysis to the outlet of a microchamber, as herein described, or in another embodiment, samples are processed separately.

In one embodiment such subsequent analysis may comprise electrophoresis, chromatography, mass spectroscopy, sequencing (for example, for the identification of particular proteins or peptides), NMR and others, as will be appreciated by one skilled in the art.

In another embodiment, screening and retrieval of cells via the methods of this invention enable detection of complex phenotypes: behaviors that vary over space (within the cell) and over time. Cells are inherently dynamical systems with specialized compartments. Timescales for relevant phenomena vary over many orders of magnitude, from the subsecond responses of cells to calcium, to the 10's of seconds for ligand-induced protein translocation, to the hours needed for mammalian cells to go through the cell cycle, and each of these timescales may be observed via the methods of this invention.

Cells (especially eukaryotic cells) are also compartmentalized systems. Transcription occurs in the nucleus, secreted proteins are processed in the Golgi, and mitochondria produce ATP. Thus, knowing a protein's location gives vital information as to its function. In addition, protein localization is dynamic; proteins shuttle from the membrane to the cytoplasm upon receptor activation, traffic through the Golgi during processing, or shuttle into the nucleus to activate transcription. Thus, temporal patterns of intracellular localization give information as to the dynamics underlying cell function; a protein of unknown function localized to the mitotic spindle during M phase is likely involved in mitosis. In another embodiment of this invention, assaying the cells via the methods of this invention, include assessment of cellular compartmentalization of a protein of interest, its spatial arrangement over time, and interaction with other cellular protein and/or nucleic acids.

In one embodiment, genetic screens can be conducted via the methods of this invention, and may use cells with fluorescent outputs, such as green fluorescent protein (GFP) or its variants [Tsien, R. Y. The green fluorescent protein. Annual Review of Biochemistry 67, 509-544 (1998)], that indicates, or reports, the presence of the phenotype of interest [Taylor, D. L., Woo, E. S. & Giuliano, K. A. Real-time molecular and cellular analysis: the new frontier of drug discovery. Current Opinion in Biotechnology 12, 75-81 (2001); Rutter, G. A., Kennedy, H. J., Wood, C. D., White, M. R. H. & Tavare, J. M. Real-time imaging of gene expression in single living cells. Chemistry & Biology 5, R285-R290 (1998)]. In one embodiment, screens of protein subcellular localization [Rolls, M. M. et al. A visual screen of a GFP-fusion library identifies a new type of nuclear envelope membrane protein. J Cell Biol 146, 29-44. (1999); Peelle, B. et al. Intracellular protein scaffold-mediated display of random peptide libraries for phenotypic screens in mammalian cells. Chem Biol 8, 521-34. (2001; Fujii, G., Tsuchiya, R., Ezoe, E. & Hirohashi, S. Analysis of nuclear localization signals using a green fluorescent protein-fusion protein library. Exp Cell Res 251, 299-306. (1999)], two-hybrid screens for protein interactions [Shioda, T., Andriole, S., Yahata, T. & Isselbacher, K. J. A green fluorescent protein-reporter mammalian two-hybrid system with extrachromosomal maintenance of a prey expression plasmid: application to interaction screening. Proc Natl Acad Sci USA 97, 5220-4. (2000)], and reporters of protein tyrosine kinase activity [Ting, A. Y., Kain, K. H., Klemke, R. L. & Tsien, R. Y. Genetically encoded fluorescent reporters of protein tyrosine kinase activities in living cells. Proc Natl Acad Sci USA 98, 15003-8. (2001)] may be effected via visual inspection of fluorescing cells, as described.

Fluorescence may also used to study the intracellular dynamics of the cells within the devices of this invention. In one embodiment, fluorescence resonance energy transfer (FRET), which is a sensitive measure of protein-protein interactions, and has been used to study everything from protein localization to kinase activity [Lippincott-Schwartz, J., Snapp, E. & Kenworthy, A. Studying protein dynamics in living cells. Nat Rev Mol Cell Biol 2, 444-56. (2001); Zhang, J., Campbell, R. E., Ting, A. Y. & Tsien, R. Y. Creating new fluorescent probes for cell biology. Nat Rev Mol Cell Biol 3, 906-18 (2002)] may be employed in the methods of this invention. In another embodiment, fluorescence recovery after photobleaching (FRAP), may be used to measure protein mobility by, in one embodiment, photobleaching a cell area and measuring the time needed to restore fluorescence from newly introduced fluorophores. In another embodiment, fluorescence correlation spectroscopy (FCS) may be used to measure protein diffusion and concentration in live cells, giving information on, in another embodiment, protein-protein interactions.

In another embodiment, morphology is another phenotypic indicator used in the methods and in accordance with the devices of this invention. In another embodiment, morphological assessment may be complemented with molecular characterization. In another embodiment, morphology is utilized in characterizing cell function, such as for example, and in another embodiment, the determination of cellular apoptosis, which may be determined morphologically, via the observation changes in cell and nuclear morphology over the time course of the process studied.

In another embodiment, one-step library screens, such as, in one embodiment, a cDNA or mutant library, of mammalian cells having undergone transient transfections with such libraries may be performed. In another embodiment, screens involving introduced genetic elements using, in one embodiment, stable transfection or in another embodiment, transient transfection with pooled libraries, may be used. In another embodiment, a device and/or method of this invention can be used to isolate single positive-responding cells for immediate genetic analysis, such as, for example, single-cell PCR.

In another embodiment, fluorescent reporters based on FRET, which experience a shift in fluorescence emission wavelength (typically blue to yellow) after activation, may be used in the devices and/or methods of this invention. The change in fluorescence (the fluorescence ratio) serves as the reporter, and in one embodiment, screening according to this aspect may be accomplished via observing the same cell twice—before and after activation—to measure the change in fluorescence. Rationally designed FRET reporters or those generated in reporter libraries via random mutagenesis may be used, in one embodiment.

In another embodiment, synthetic genetic regulatory modules introduced into, for example, *E. coli* may be used to investigate genetic regulation and fundamental cell biology, via the methods of this invention. In one embodiment, combinatorial techniques to generate plasmids randomly encoding differing two-input (the small molecules IPTG and aTc) and one output (a GFP reporter) logic functions may be used as described [Guet, C. C., Elowitz, M. B., Hsing, W. & Leibler, S. Combinatorial synthesis of genetic networks. Science 296, 1466-70. (2002)]. in one embodiment, similar library-based approaches could be extended to dynamic (or even localization) circuits (such as variations on the original repressilator) where cells are easily isolated after extended dynamic monitoring.

In another embodiment, phage display is used to engineer antibodies or other proteins with specific properties (e.g., high-affinity binding of ligand), whose binding may be determined using the devices and via the methods of this invention. In one embodiment, engineered enzymes, which produce diffusible products may be assessed via the methods and utilizing the devices of this invention, such as via, in one embodiment, visualization of a ligand that became fluorescent after enzymatic processing, wherein one could screen for a diffuse fluorescent cloud around cells and thus assay enzymatic activity. In one embodiment, according to this aspect, strongly fluorescent clouds would then indicate enzymes with rapid kinetics, which could then be isolated and undergo further rounds of evolution.

In another embodiment, combining fluorescence reporter output (fluorescence intensity) with localization greatly enhances the capability of cell-based screens. In one embodiment, high-throughput genetic screens for investigating the secretory pathway, for example, with a VSVG-GFP reporter could be used to find proteins that affect various steps in this pathway. In one embodiment, specific inhibitors of Golgi-to-membrane trafficking, such as for example, secramine, may be isolated via chemical genetic screen, performed via the methods of this invention. In one embodiment, a translocation-based screen may be conducted using a device and/or via the methods of this invention. In one embodiment, a fluorescent NFAT reporter that translocates to the nucleus upon activation may be used to screen a cDNA library for proteins that disrupt this pathway, wherein the imaging and isolation of positive-responding cells is conducted using the devices and/or via the methods of this invention.

In another embodiment, the microfabricated format of the devices of this invention may be utilized to functionally probe cells, in conjunction with other cellular probe machinery. In one example, the sorting devices of this invention may be modified to include the ability to perform on-chip patch clamping, which allows one to functionally screen transiently transfected ion-channel libraries. In another embodiment, real-time nanoscale sensors and other microfluidic-based technologies may be incorporated within the devices of this invention.

In some embodiments of the methods of this invention, the step comprising detecting the particles comprises assaying the particles, and in some embodiments, the assigning of at least a subset of the detected particles for removal and/or for patterning on a substrate is a function of the results of the assay. Such assigning and conveyance and/or removal may be accomplished on any appropriate time scale, from fractions of a second to seconds, to minutes, hours, days, weeks, months, or even years.

In some embodiments, the methods of this invention employ an optical force source, which is a near infrared laser. In some embodiments, the methods of this invention employ a detection system which is an optical detection system, which in some embodiments, comprises a microscope, and/or in some embodiments, comprises a light source and a detector. In some embodiments, the detector detects scattered light, or in some embodiments, the detector detects fluorescence emissions.

In some embodiments, the apparatus used in accordance with the methods of this invention is a modular system, and in some embodiments, the sorter may be readily removed from or inserted into said apparatus. In some embodiments, the methods of this invention comprise the step of evaluating or assessing the sorted particles and prior to assigning which particle or particles for conveyance or removal, the sorter is removed from the apparatus and maintained under desired conditions which differ from that present in the apparatus, for any desired time-frame.

In some embodiments, the methods of this invention make use of an apparatus further comprising channels linked to the outlet of the sorter, such that sorted particles are conveyed from the sorter through the channels. In some embodiments, the apparatus comprises a second substrate comprising the sorter and the channels and in some embodiments, the particles are conveyed to desired regions on the second substrate via the channels.

In another embodiment, this invention provides a method of particle patterning on a substrate, said method comprising:
    applying a fluid comprising particles to an inlet of a particle sorting apparatus, said apparatus comprising:
        a particle sorter comprising:
            a first substrate comprising two or more chambers, wherein said chambers are sized to accommodate a desired number of particles;

at least one inlet for the introduction of fluids into said sorter; and at least one outlet for the conveyance of fluids out of said sorter;

a second substrate comprising said sorter and channels linked to said outlet of said sorter;

a detection system operationally connected to said sorter; and an optical force source operationally connected to said sorter;

detecting said particles and assigning at least a subset of said detected particles for conveyance from said sorter to at least a portion of said channels; and applying an optical force under flow to said particles assigned for conveyance whereby said optical force applied under flow conveys said particles to said channels and cessation of said optical force and said applied flow allows for patterning of said particles on said second substrate.

In another embodiment, this invention provides a method of particle patterning on a substrate, said method comprising: applying a fluid comprising particles to an inlet of a particle sorting apparatus, said apparatus comprising:

a particle sorter comprising:

a first substrate comprising two or more chambers, wherein said chambers are sized to accommodate a desired number of particles;

at least one inlet for the introduction of fluids into said sorter; and at least one outlet for the conveyance of fluids out of said sorter;

a second substrate comprising said sorter and channels linked to said outlet of said sorter;

a detection system operationally connected to said sorter; and a controllable optical force source operationally connected to said sorter applying an optical force to said particles having a beam waist about comparable to a diameter of said particle whose sorting is desired;

detecting said particles and assigning at least a subset of said detected particles for conveyance from said sorter to at least a portion of said channels; and applying an optical force under flow to said particles assigned for conveyance whereby upon applying fluid to said device, said particles are accommodated in said chambers and application of said optical force to said subset of particles under flow conveys said subset of particles to desired locations on said second substrate, thereby patterning said particles on said second substrate.

In one embodiment, the term patterning refers to the specific deposition of at least one desired material, such as, in some embodiments, particles, or cells, at a desired location, on a substrate.

The devices and/or methods of the present invention can be used, in some embodiments, to pattern thousands of cells, with single-cell resolution, and concurrently be so constructed so as to allow the cells room to grow.

In one embodiment, the second substrate, onto which the material is patterned, may be coated, or associated with another material, or another layer of cells. When cells are patterned onto the second substrate, in some embodiments, they can attach after a few hours and proliferate.

In one embodiment, assay or analysis may be conducted subsequent to cell patterning, spreading, proliferation, or a combination thereof. In one embodiment, the assay is a diagnostic assay.

In one embodiment, the cells are engineered to express at least one desired molecule, or in another embodiment, the cells are contacted with a library of molecules prior to loading of the cells. In one embodiment, the cells are assayed to determine efficacy of a molecule within said library, which in one embodiment, is a drug. In one embodiment, the cells are stem or progenitor cells, and in one embodiment, the cells are engineered to express at least one desired protein. In one embodiment, the cells are cultured under conditions promoting expression of the protein, and in one embodiment, the conditions promote tissue engineering as a function of expression.

In one embodiment, the devices and/or methods of the invention modulate cell-cell signaling by patterning single cells in grids of different configurations.

In one embodiment, cells or particles are assayed when positioned on the first or second substrate, or both. In some embodiments, the components of the device are selected such that minimal background contribution of the materials is contributed to the readout of the assay. In some embodiments, such choice in material is a reflection of the reagent used. In one embodiment, the reagent may comprise is an antibody, a nucleic acid, an enzyme, a substrate, a ligand, or a combination thereof, which in turn may be coupled to a detectable marker, which in another embodiment is a fluorescent compound. In one embodiment, according to this aspect of the invention, the substrates may be comprised of a transparent material, and in another embodiment, analysis is carried out using automated microscopy, and may comprise the application of, for example, fluorescence microscopy, following the sort prior to and in some embodiments, subsequent to the patterning of the particles or cells. In some embodiments, comparative differences in the obtained readout are useful.

In another embodiment, such assay may make use of microscopy, which in turn can be coupled to the devices of the invention, and provide for automated imaging and phenotype acquisition as part of the methods of this invention. In one embodiment, commercially available, automated microscopes by Zeiss, Nikon, etc. which enables the user to control the objectives, fluorescence filters, x-y stage, z-axis (autofocus), diaphragms, etc may be used. According to this aspect, appropriate control software (e.g., Metamorph) may be used, in another embodiment, to set up a timelapse protocol repeatedly taking brightfield and fluorescence pictures of an arbitrary set of fields at arbitrary time intervals.

In one embodiment, the use of two-photon microscopy will be used in order to give greater fluorescence sensitivity, or, in another embodiment, quantum dots may be used for high-brightness live-cell labeling.

In one embodiment, a combination of general assays to test overall long-term effects of cellular manipulations in the patterning methods of this invention may be conducted, which may comprise molecular analysis of the stress response using, for example, immunofluorescence or RT-PCR. In one embodiment, stress responses may be determined via the characterization of changes in both nuclear accumulation and mRNA levels in response to manipulation on-chip. In one embodiment, the devices and/or methods of this invention find application in various screens. In one embodiment, the screen may be a genetic screen, which in one embodiment has three fundamental steps: 1) alteration of the genetic program of the cell, 2) patterning the altered cell under desired conditions and 3) observation and/or identification of altered phenyotype in the cell as a consequence of the genetic changes. In some embodiments, the method will enable the determination of the elements responsible for the displayed phenotypes. In one embodiment, alteration can be accomplished using the natural (background) mutation rate, or, in another embodiment, inducing mutations with chemicals or UV light, or in another embodiment, introducing exogenous pieces of DNA (e.g., transfection), or, in another embodiment, using small molecules or siRNAs to alter protein function or, in another embodiment, protein expression. In one embodiment, specific patterning of the altered cells, with the ability to control the cellular microenvironment and its downstream effects will dramatically enhance the reach of genetic screens.

In another embodiment, the methods and/or devices enable the determination of behaviors that vary over space and over time. Cells are inherently dynamical systems with specialized compartments. Timescales for relevant phenomena vary over many orders of magnitude, from the subsecond responses of cells to calcium, to the 10's of seconds for ligand-induced protein translocation, to the hours needed for mammalian cells to go through the cell cycle, and each of these timescales may be observed via the methods and/or devices of this invention.

In another embodiment, the devices of this invention find application in the construction of optical colored displays. According to this aspect of the invention, and in one embodiment, a solution comprising hollow particles e.g. vesicles are individually introduced to wells of the first substrate. The vesicles encapsulate a labeled marker, for example, a red dye molecule. The substrate is flipped over a transparent surface and the solution is dried out causing the vesicles to break and release the red dye onto the surface in positions that follows the spacings in the substrate well array. The substrate is cleaned and filled with vesicles that carry blue dye molecules. The substrate is aligned with one well length shift to its former position with respect to the surface. The process is repeated yielding a square area of blue dye molecules next to the square area of the red dye molecules on the transparent surface. The process can be repeated with additional colors to yield a display exhibiting an array of pixels each contains a set of different colors. Each pixel can be later addressed electronically or optically by attaching an appropriate probe to each pixel area.

In another embodiment, the devices and/or methods of this invention may find application in the detection of cell signaling events. In some embodiments, such signaling events are stimulated by proximity, for example, early signaling events in white blood cells when in proximity to a pathogen may be readily determined using the methods and/or devices of the invention. In one embodiment, the first particle sorted may comprise patterning of individual macrophages. The method may also entail sorting of specific for example, mutagenized, or library transformed pathogens, which in turn are patterned onto the region wherein the macrophages were previously patterned. In another embodiment, varying numbers of bacterial cells, for example, are patterned, enabling the positioning of a desired number of pathogens, and cell signaling in the macrophages is determined as a function of bacterial cell number in proximity to the macrophages. In another embodiment, other signaling events in cells may be determined as a function of environmental conditions, cell density, etc. For example, bacterial cells may be patterned at varying density on the second substrate, and the initiation of quorum sensing may then be determined.

In some embodiments, the methods and/or devices may be used to form multiple patterns of particles/cells. According to this aspect, and in one embodiment, the methods and/or devices may be used to pattern a first cell type or particle onto the substrate, and subsequently pattern an additional cell type and/or particle onto the substrate. In some embodiments, multiple rounds of patterning are envisaged. In some embodiments, the second patterning is atop the first cell or particle patterned, or in another embodiment, the second patterning is shifted over by a discrete length, for example one cell or particle length over, so as to produce, for example, a checkerboard of different cells or cell/particle, or particle/particle arrangements. In some embodiments, variation in multiple patterning steps enables arrangements of specific lines/rows of different particles/cells on a single array. In some embodiments, such patterned arrays with repeat patterning steps may be accomplished utilizing the same first substrate twice, or in some embodiments, using multiple first substrates, patterning cells/particles onto the same second substrate.

In some embodiments, this enables patterning of cells onto substrates comprising cells or particles which have not been patterned. Some applications of this principle may include patterning single bacterial cells onto monolayer of immune cells, for example, where the bacterial cells are for example engineered to express a library, which comprises mutations which affect the pathogenesis of the organism.

In some embodiments, the particles for use with the devices and/or methods of this invention comprise a drug, an antibody, a nucleic acid, or any compound of interest. The compound may serve as a probe for a particular function, or to determine expression, or in other embodiments, to treat a particular condition. In some embodiments, such compound-associated beads, which may be physically attached, or attracted to the beads by non-covalent association, may be patterned onto individual cells, multiple patterned arrangements, monolayers of cells, non-patterned cell groupings, etc. There is no limitation to the application of the compound-associated bead to any substrate, in this invention.

In some embodiments, cells can be patterned onto electrodes, and can in turn find application as biosensors, as is well known in the art, for example, as described in U.S. Application Publication Number 20050095630; U.S. Application Publication Number 20050014201; U.S. Application Publication Number 20040048241, and others, as will be appreciated by one of skill in the art.

In some embodiments, the methods and/or devices may be used to determine the effects of specific geometries on cell growth. For example, the particle patterning device may comprise a second substrate with a non-flat surface.

In some embodiments, the devices and/or methods of this invention may be used to modify surfaces of a substrate.

These and other aspects of the present invention will be further appreciated upon consideration of the following Examples, which are intended to illustrate certain embodiments of the invention but are not to be construed as limiting in scope.

EXAMPLES

Materials and Methods

Construction of Sorting Device

A two-layer SU-8 process was used to fabricate silicon wafer masters for PDMS molding. SU-8 photoresist was spin-coated onto a silicon wafer. The photoresist was exposed under ultraviolet radiation (UV) under a mask to yield features which, when molded, define a flow chamber. The first SU-8 layer (105 μm-thick, 1600 rpm, SU-8 2050, Micro-Chem, Newton, Mass.) defined flow channels, while the second SU-8 layer (35-μm-thick, 2750 rpm, SU-8 2035, Micro-Chem) defined arrays of 25- and 30-μm-diameter posts to pattern microwell arrays into the bottom of the flow channels after molding. The resist was developed, yielding a patterned SU-8 wafer.

Wafers were silanized for 24 h with (tridecafluoro-1,2,2-tetrahydrooctyl)-1-tricholorosilane (T2492-KG, United Chemical Technologies, PA) evaporated in a dessicator with the masters to decrease adhesion of PDMS to the master during molding. After mixing PDMS (Sylgard 184, Dow Corning, Mich.) at a 10:1 base:curing agent ratio and degassing the PDMS for ~1 hour in a dessicator, the PDMS was poured onto the wafer, cured the PDMS for 2 h in a 65° C. convection oven, and peeled the cured PDMS off of the master, achieving a PDMS thickness of ~2 mm. Using diamond-tipped drill bits (Tripple Ripple product line, CR Laurence, Calif.), tubing ports were drilled into 1-mm-thick glass slides and glued PEEK tubing (1532, Upchurch Scientific, WA) to the ports using epoxy (High performance Epoxy, 99393, Loctite, Avon, Ohio). After exposing the PDMS layer to oxygen plasma (PDC-001, Harrick Scientific, Ossining, N.Y.), the PDMS was bonded to the glass slide, resulting in a sealed flow chamber with a microwell array patterned into the chamber floor. After bonding, the chip was placed in a convection oven set to 65° C. for 12 h to accelerate PDMS hydrophobicity recovery after plasma bonding to facilitate later adsorption of bovine serum albumin (BSAC). Cells were found to adhere less to BSA-treated hydrophobic PDMS than to BSA-treated hydrophilic PDMS, suggesting that BSA adsorption might be similarly enhanced to hydrophobic PDMS.

In some embodiments of the microfluidic chip had three critical fluid connections. One connection was for loading the cell suspension, one was for injecting a flushing buffer, and the other was an output connection which can be toggled with a simple off-chip valve. In one aspect, syringe pumps drive both inputs via 4-way valves (V-101D, Upchurch Scientific) which allowed for switching between the syringe pump medium and another fluid (ethanol as illustrated) in a bubble-free manner. An injection valve (V-451, Upchurch Scientific) with a 100 µL PEEK sample loop was used to inject cell suspensions into the device.

Optics and Laser Incorporation

All experiments utilized an upright Axioplan 2-MOT (Zeiss, Thornwood, N.Y.) microscope with a computer-controllable motorized stage (999000, Ludl). For fluorescence imaging, an EXFO X-Cite 120 fluorescence source (EXFO Photonic Solutions, Inc., Richardson, Tex.), Chroma 41001 FITC, 41007a Cy3, and 31004 Texas Red fluorescence filter sets (Chroma Technology Corp., Rockingham, Vt.) were used. An LaVision Imager 3 QE CCD digital camera (LaVision GmbH, Goettingen, Germany) was used for all image recording. The computer-controllable laser diode system utilized a 980-nm fiber-coupled semiconductor diode laser (3CN00283AL, Avanex, Fremont, Calif.) capable of outputting up to 290 mW of single-mode output power. A butterfly package holder (LM14S2, Thorlabs, Newton, N.J.) interfaced with the diode and laser output levels were controllable using a laser diode/thermoelectric cooler (LD/TEC) controller (LDTC 2/2, Wavelength Electronics, Bozeman, Mont.). The LD/TEC controller was controlled remotely through a USB-interfaced A/D and D/A converter (USB-1408 FS, Measurement Computing, Norton, Mass.) via the MatLab Data Acquisition Toolbox (MathWorks, Natick, Mass.).

A simple cage-mounted collimation/focusing apparatus allowed simple incorporation of the fiber-coupled laser into the microscope. The assembly was positioned underneath the microscope stage using optomechanics mounted on switchable magnetic bases for straightforward insertion and removal of the laser. To collimate and focus the beam, identical 0.15 NA aspheric lenses (C280TM-B, Thorlabs) were used. During laser exposures, microscope components were protected from IR damage by using a filter cube with 3-mm-thick KG5 glass in the fluorescence excitation and emission paths (Chroma Technology) and 2-mm-thick KG5 glass in two filter sliders leading to the light sources (FIG. 2-B). Eyepiece transmission was shut off during laser exposures, and a 20× Achroplan objective (440040, Zeiss) was used for all imaging during laser exposure. The switcher in the dual video output tube of the microscope diverted imaging from the LaVision CCD to a Bullet CCD connected to a television during laser exposures whose visualization was desired, protecting the LaVision CCD. When recording videos, the Bullet CCD was replaced with a FireWire CCD (Fire-i 400, Unibrain, San Ramon, Calif.), again in the interest of protecting the LaVision CCD from damage.

Computer Automation and Interfacing

MatLab was utilized to create software allowing the simultaneous interfacing of the laser, microscope, and motorized stage. The software facilitated automatic scanning over the microwell array and recording of multi-wavelength fluorescence/brightfield images of the entire array. The software also facilitated rapid image-based inspection of individual array sites and easy marking of sites of interest. Subsequently, the software generated a list of marked sites and allowed for rapid, automatic return to those sites for removal of target cells. The software isolated the user from bookkeeping and registration of large arrays. The interface allowed for natural extension of the software to incorporate automatic image-based selection of cells of interest through image algorithms.

Device Preparation

Prior to all experiments, the output valve was opened and an ethanol mixture (80% ethanol, 20% de-ionized water) was flowed into both inputs to facilitate device filling and sterilization. After closing the output path, the microwells were degassed by applying pressure to both input syringes, driving bubbles in the microwells out through the PDMS. After filling the device, the output was opened and the device flushed with phosphate-buffered saline (PBS) (14190, Gibco, Carlsbad, Calif.). 75 mg/mL bovine serum albumin (BSA) fraction V solution prepared in PBS (15260, Invitrogen, Carlsbad, Calif.) was then flowed into the cell injection path and filled the device. The BSA remained in the chamber at room temperature for 1 h to adsorb to the PDMS surface to help block cell adhesion in the subsequent experiment. Afterwards, the chamber was flushed with PBS.

Cell Culture and Preparation

Cell incubation conditions were 37° C., 7.5% $CO_2$, in a humidified atmosphere. Cultured BA/F3 pro B cells and WeHi-3B myelomonocytic leukemia cells (Whitehead Institute, Cambridge, Mass.) were used. B cell culture medium was RPMI 1640 (21870, Gibco), supplemented with 10% v/v fetal bovine serum (FBS) (SH30088.03, Hyclone, Logan, Utah), 2% v/v L-glutamine (25030, Gibco), 1% v/v penicillin-streptomycin (15140, Gibco), and 10% v/v WeHi-3B conditioned medium. Leukemia cell medium was Iscove's modified Dulbecco's medium (IMDM) (12440, Gibco) supplemented with 10% v/v FBS, 1% v/v penicillin-streptomycin and 25 □M 2-mercaptoethanol (21985, Gibco). WeHi-3B conditioned media was prepared by collecting media from WeHi-3B cells grown in T75 flasks (3 days after seeding), spinning media down at 1000 rpm for 7 minutes, and collecting the supernatant. After collection, the media was filtered through a 0.2 □m vacuum filter bottle, aliquotted the media, and stored at −20° C. for future use in B cell culture.

Two lines of MCF7 epithelial breast cancer cells were cultured, one of which was transfected with a construct expressing the red fluorescent protein mCherry[16] fused to the mouse ornithine decarboxylase PEST sequence and three copies of the SV40 large T-antigene nuclear localization sequence (NLS) under the control of the p21 promoter. Selection with blasticidin established a stable, clonal cell line. A second line was not transfected. MCF7 culture medium for the non-transfected line was RPMI 1640 supplemented with 10% v/v FBS, 1% v/v L-glutamine, and 1% v/v penicillin-streptomycin. Culture medium for the transfected cell line additionally contained 5 □g/mL blasticidin (ant-b1-1, InvivoGen, San Diego, Calif.).

For experiments using CellTracker dyes, either CellTracker Green CMFDA (C7025, Invitrogen) or CellTracker Orange CMRA (C34551, Invitrogen) were used at concentrations of 5-10 □M, and stained per product datasheet, unless noted otherwise. Prior to injection into the device, cells were re-suspended in standard culture medium at total cell concentrations of $1\text{-}10 \times 10^6$ cells/mL. HL-60 cells were similarly stained.

Cell Experiments

For whole-cell fluorescence sorting, a majority of cells with CellTracker Green and a minority with CellTracker Orange in a ratio of ~50:1 to demonstrate the removal of rare cells from a background population. The two populations were mixed before injection into the device. For localization-based sorting, a non-transfected population of MCF7 cells was double-stained with CellTracker Green (2.4 µM) and CellTracker Orange (0.4 µM), staining the entire cell. The double-stained population was mixed with a population of transfected MCF7 cells expressing nuclear-confined mCherry fluorescence. The low concentration of CellTracker Orange was used to roughly match the mCherry fluorescence levels in the transfected cells for demonstration purposes. Alternatively, a single population of HL-60 cells in 20 mL of bovine-calf-serum-containing HL-60 media in a cell culture dish for 15 minutes with Hoechst added to a final concentration of 5 µg/mL [Hoechst 33258, Molecular Probes] to stain the nuclei of the cells. All cells were washed in Dulbecco's phosphate buffered saline (PBS), (Gibco).

A fraction of cells was placed in a culture dish containing PBS, while remaining cells were placed in a culture dish containing bovine-calf-serum-containing HL-60 media. Concanavalin A (Con A) (Alex Fluor 488 conjugate, Invitrogen) was added to the cells in the PBS-containing dish to achieve a final concentration of 50 µg/mL. The Con A staining was preferentially confined to the membrane. The cells were incubated for 20 minutes. The Con A-stained cells were washed twice in PBS and recombined with the cell population stained solely with Hoechst, yielding a mixture of nuclear– and nuclear+membrane-stained cells. The two populations were recombined in fresh bovine-calf-serum-containing HL-60 media until injection into the device.

Application of Cells to the Sorting Device

HL-60 cells were applied to the sorting device in concentrations of approximately $1 \times 10^6$/mL in bovine-calf-serum-containing HL-60 media and cells were distributed within the wells of the device. Prior to injection with cells, PBS, was injected into the device to flush it, ethanol injections followed for cleaning the device, and then rinses were conducted with additional PBS. 7.5% bovine serum albumin (BSA, Invitrogen) in PBS was injected into the chamber and incubated for 45 minutes at 37° C., to minimize HL-60 adherence to the PDMS. The device was flushed with PBS in order to clear cells outside wells via flow. PBS was left in the chamber during fluorescence imaging in order to reduce background fluorescence levels.

Cell Sorting

Cells were imaged by fluorescence microscopy technique to locate cells of interest. A 514 nm argon laser (power levels between 100-180 mW) was coupled to the device, and the beam was focused onto individual wells through a 10× objective (Edmund Optics) with a nominal numerical aperture (NA) of 0.25, though the focused beam NA was approximately 0.08-0.1 to produce a spot size roughly equivalent to size of the HL-60 cells, which were approximately 8-10 µm in diameter. Beam diameters larger than the target waste power, as power would not be incident on the target, and beam diameters smaller than the target produce smaller net pushing forces due to optical gradient forces opposing the pushing of the target. Additionally, spot sizes smaller than the target produce unnecessarily high local intensity spots, potentially damaging cells. Upon focusing by the laser beam, targeted cells were levitated out of their wells by the optical scattering force. After levitation of a target cell, the laser was turned off, and the levitated cell was removed by the flow field at a flow velocity of approximately 200 µm/s for downstream collection.

Alternatively, cells were injected into a 100 □L sample loop via the injection port/valve assembly and the cell suspension was pumped into the device at a flow rate of 100 µL/min with the syringe pump. After the cell suspension filled the device, flow was stopped for ~5 min., allowing cells to sediment into the wells. Fresh media was pumped through the second syringe pump into the purging input of the device at ~20 µL/min, removing cells residing outside the microwell array. Using the second input to provide the purging media avoided introduction of residual cells still in tubing leading to the cell loading input. Software developed for this purpose as described above was used to scan the entire array, inspect and mark individual sites, and return to specific sites to remove cells using the laser. During removal, a flow rate of 5 µL/min was used and ~100 mW of laser power was applied to each cell until the cell was levitated high enough that the flow displaced the cell and carried it downstream.

Example 1

Principles of Operation of an Embodiment of an Opto-Fluidic Particle Sorter

Figure 1B:
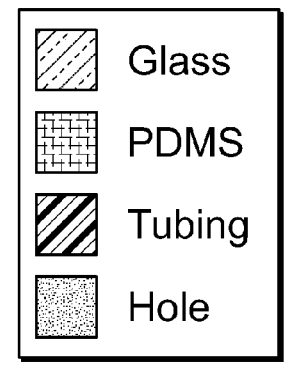
FIG. 1B schematically depicts one embodiment of a packaging scheme for the sorter. (1) Glass slide. (2) Diamond drill bit used to drill holes in slide. (3) Helper slide placed under drilled slide; tubing mounted through drilled slide and joined using epoxy. (4) Helper slide removed. (5) PDMS poured, degassed, cured, removed. (6) PDMS bonded to helper coverslip to add mechanical rigidity. (7) Complete bonded structure.
Figure 1B:
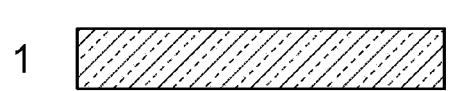
Figure 1B:
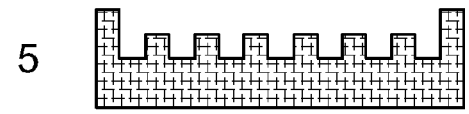
Figure 1B:
Figure 1B:
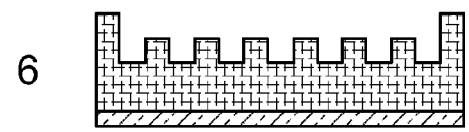
Figure 1B:
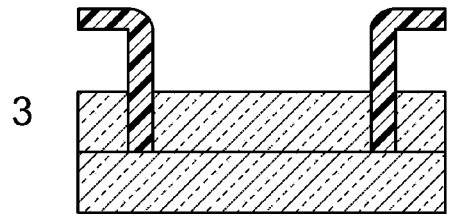
Figure 1B:
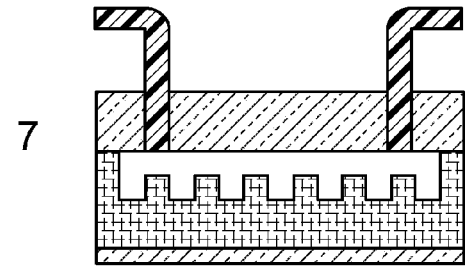
Figure 1B:
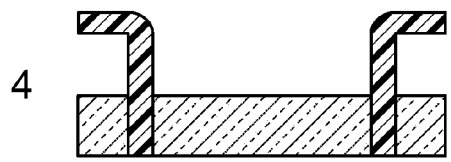
Figure 1C:
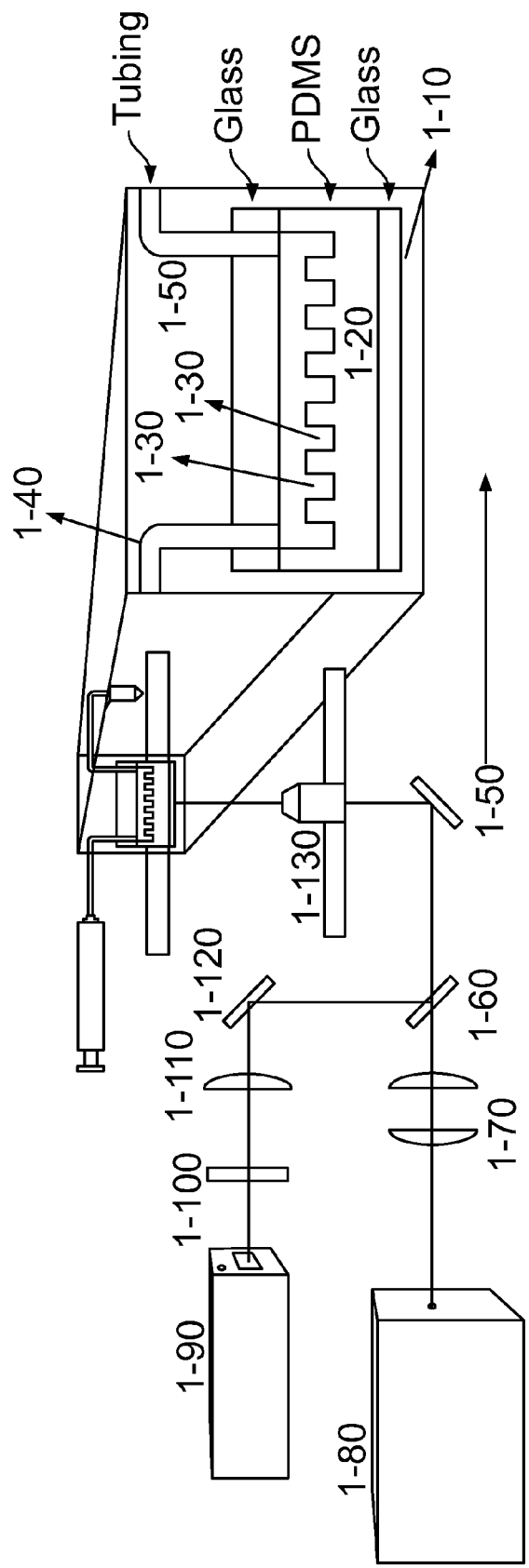
FIG. 1C schematically depicts one embodiment of the device in terms of its structure and layout. The sorter (1-10) comprises an array (1-20) having a series of chambers (1-30), an inlet (1-40) and an outlet (1-50). The sorter is coupled to a detector, in this case an optical detector and an optical force source, in this case a laser (1-80), which can be focused on the array via the use of mirrors (1-50, 1-120, respectively) a beam splitter (1-60) beam expander (1-70) tube lens (1-110), filter (1-100) and an objective (1-130), for example, a 10× objective having a 0.25 numerical aperture.
Figure 1D:
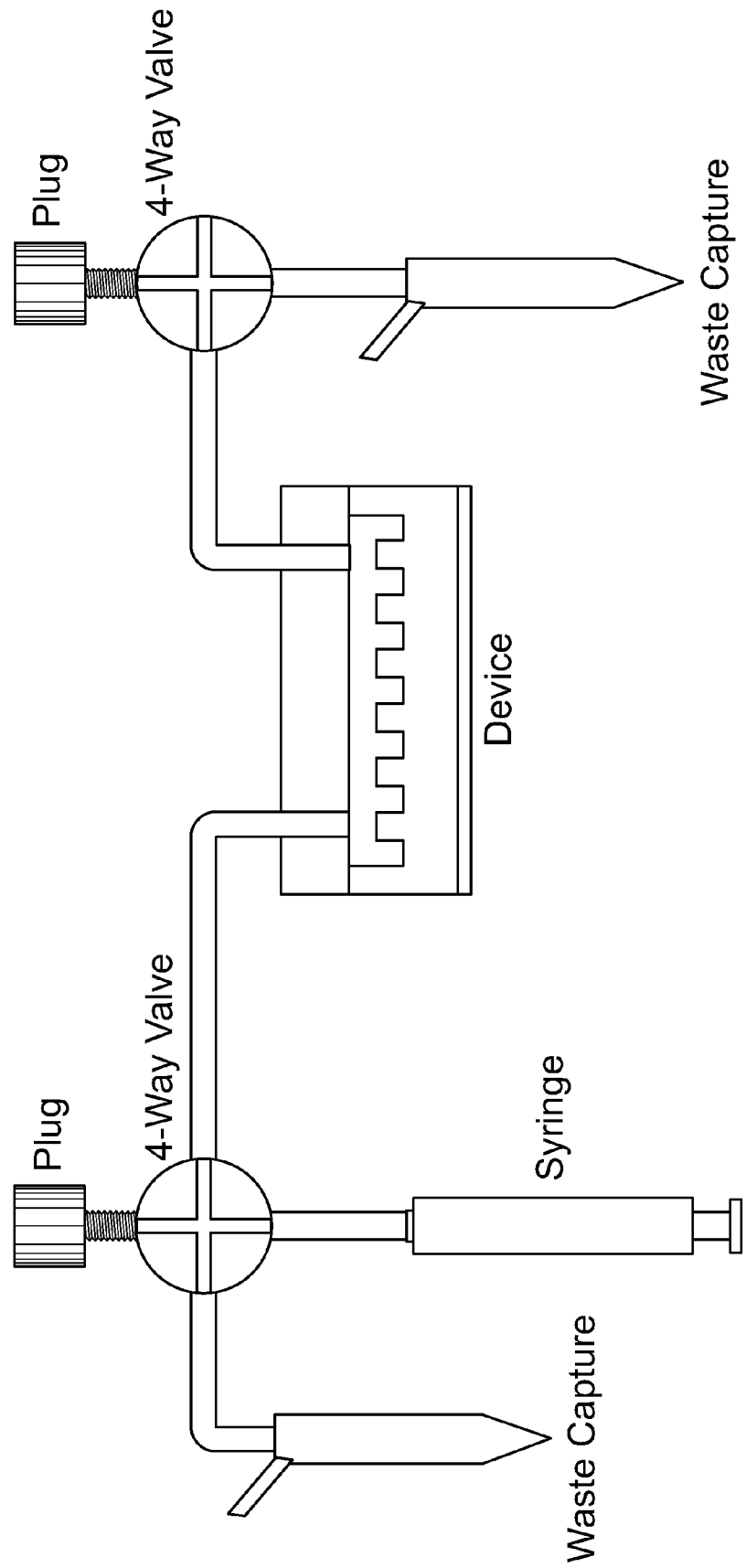
FIG. 1D schematically depicts an embodiment of the layout of a microfluidic network and interface (unions & luers not drawn), which can be used as part of an apparatus of this invention. Syringes filled with various fluids can be applied, and exchanged, and flow controlled using for example, a 4-way valve syringe path for, inter-alia, waste capture. Valves may regulate flow and aid in maintaining desired conditions during device transport.

A microfluidic chamber comprising a PDMS well array was constructed as outlined in FIG. 1A. One embodiment of a packaging scheme of the constructed device is schematically depicted in FIG. 1B. The chip can be coupled to a detection/analysis apparatus, for example, a fluorescence microscope and CCD camera and optical sorting module, the laser, as schematically depicted in FIG. 1C, and an embodiment of a layout of the microfluidic network and interface is depicted in FIG. 1D.

Figure 2A:
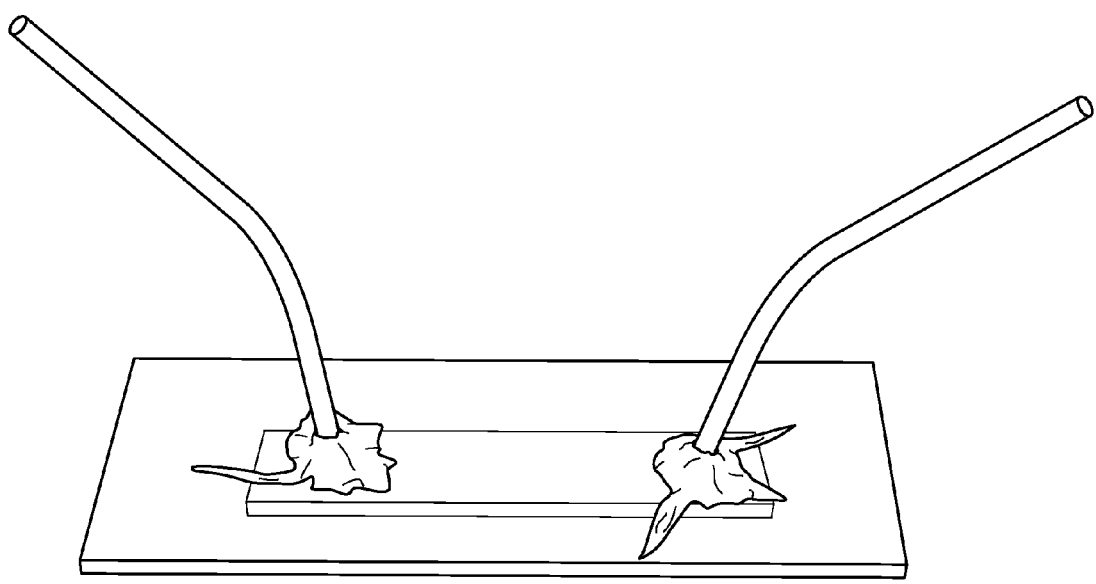
FIG. 2A is a photograph of one embodiment of a device, which was constructed as described in the Examples herein.
Figure 2B:
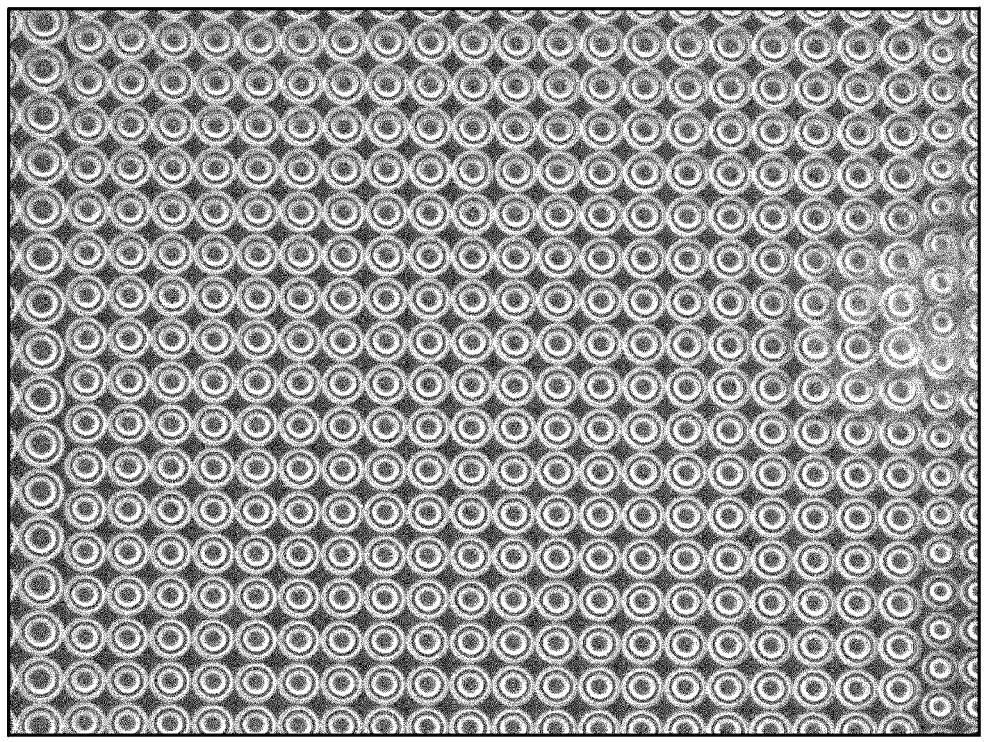
FIGS. 2B, 2C shows embodiments of the well arrays formed, which can be constructed with wells of varying diameter (for example, as shown herein, 25, 30 and 35 or 60, 70 and 80 micron, respectively).
Figure 2C:
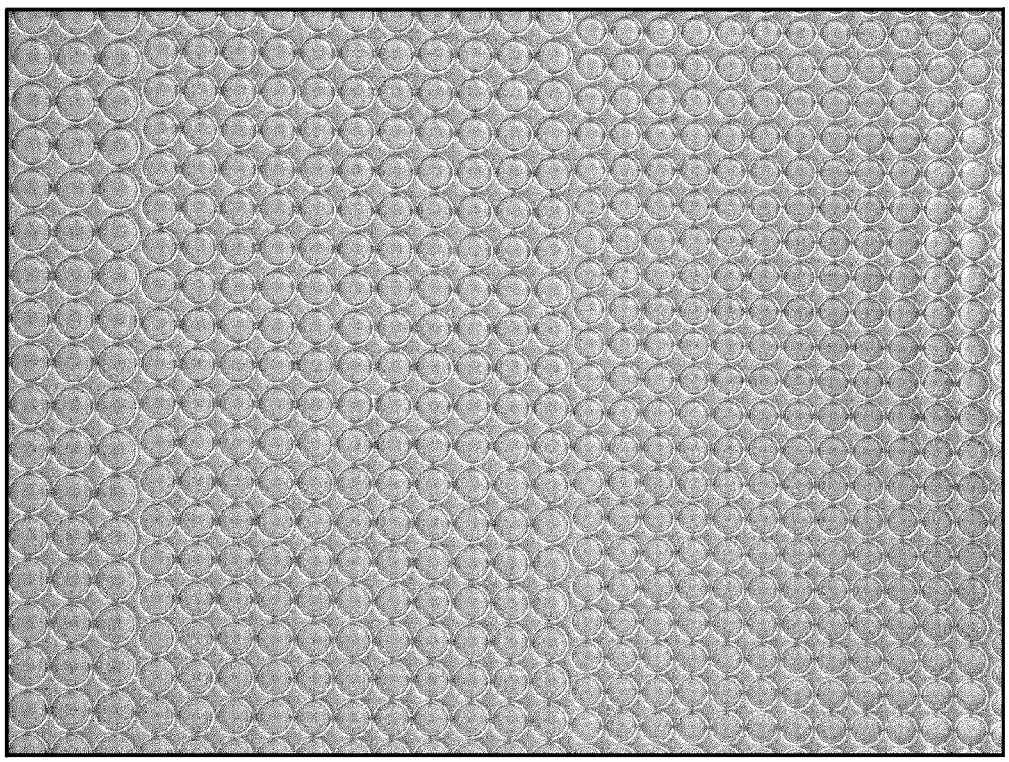

FIG. 2A shows one embodiment of a device, which was constructed herein. FIGS. 2B, 2C shows embodiments of the well array, which can be constructed with wells of varying diameter (25, 30 and 35 or 60, 70 and 80, respectively).

Figure 2D:
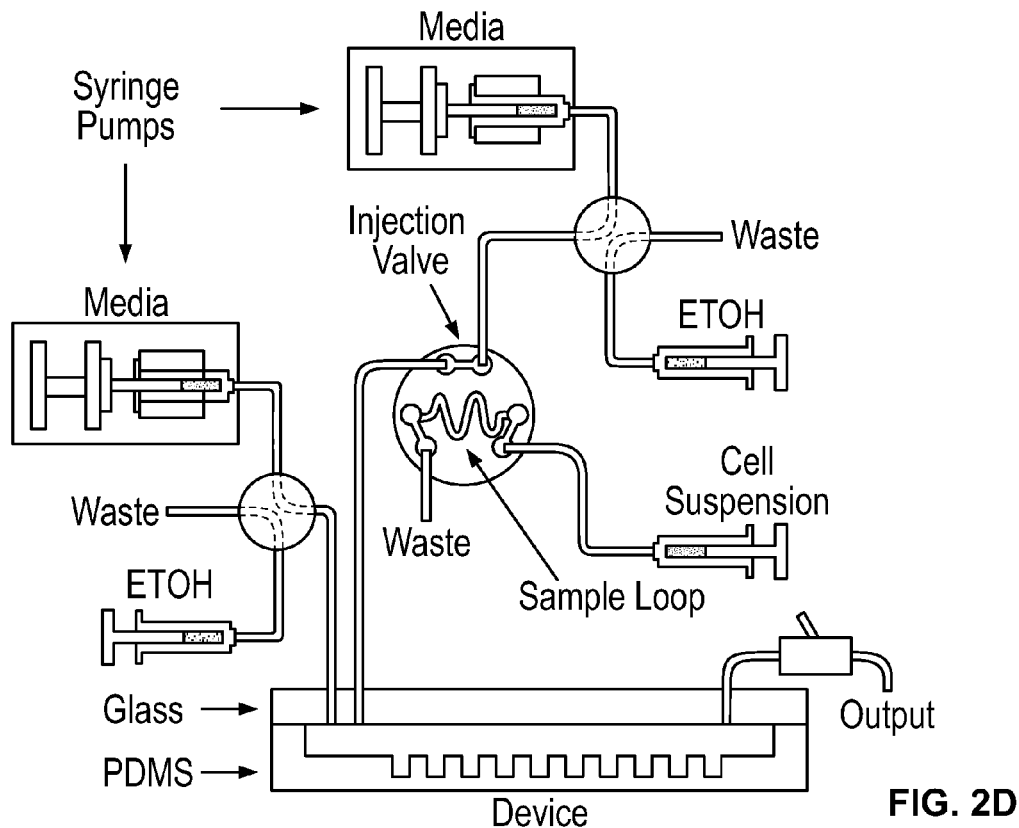
FIGS. 2D, 2E show an embodiment of an apparatus comprising an embodiment of a microfluidic device of this invention. (D) Support fluidics. We use syringe pumps and an injection valve to load cells into our device. (E) Incorporation into a standard automated upright microscope. A 3-axis stage mounted on a switchable magnetic base allows rapid incorporation and alignment of the laser. Use of KG5 filter glass throughout the microscope protects components from laser damage.
Figure 2E:
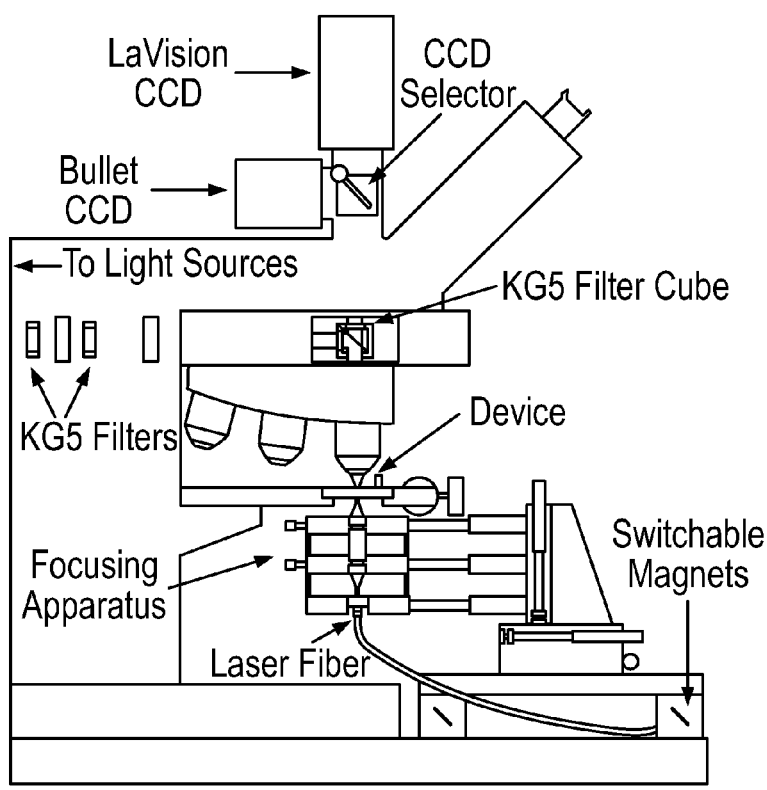

FIG. 2D shows another embodiment of a device of the invention. The support fluidics and their integration are depicted in this embodiment of the device of the invention. Incorporation of an embodiment of the device into a standard automated upright microscope is shown in FIG. 2E. A 3-axis stage mounted on a switchable magnetic base allows rapid incorporation and alignment of the laser. Use of KG5 filter glass throughout the microscope protects components from laser damage.

Passive cell loading via sedimentation and subsequent flushing deposits single cells, or a desired number of cells in individual wells (FIG. 3A-B). The number of cells deposited can be fixed or random, and in some embodiments is biased by controlling cell concentration and well size.

Such a setup can provide for visualizing cells using any desired microscopy technique, such as, for example, phase contrast microscopy or fluorescence microscopy, or others, and positions of cells of interest are noted. Cells whose removal from the device is desired can be removed via application of an optical scattering force by focusing the laser onto the particular cell, resulting in the cell's egress into the flow (FIG. 3C-D).

According to this embodiment of the invention, the focusing of the laser into a low-divergence shape results in gradient forces that are significant in the lateral direction, but miniscule in the axial direction. In this case, the radiation pressure induced onto the cell by photon scattering is greater than the axial gradient force. Therefore, when the beam is focused onto a cell, the lateral gradient force quickly translates the cell to the lateral beam center, and the scattering force causes the cell to levitate axially.

In some embodiments, such cellular manipulation offers advantages over traditional optical tweezers. For example, while many high-numerical aperture lenses used for 3-D optical trapping must be used through substrates of specified (usually thin) thickness and have short working distances, the low-divergence of the beam allows for longer working distances and actuation ease is much less sensitive to substrate thickness. In the embodiment described hereinabove, the beam was readily focused through a ~2 mm PDMS substrate whose thickness varied throughout the device and achieved adequate actuation. Another example of an advantage to the devices described herein is that the focused spot sizes are larger than those typically used in optical tweezers applications, which can lower peak optical intensities and thus mitigate cell damage. Selective levitation of a single cell from a microwell without perturbing cells in neighboring wells was readily accomplished, for example as demonstrated in the following example.

In one embodiment of such a device, the optical intensity and energy-density levels applied to the cells are orders of magnitude below those found harmful in conventional, high-numerical aperture optical tweezers, and thus such approach is unlikely to damage the applied cells.

Example 2

Principles of Operation of an Embodiment of an Opto-Fluidic Particle Sorter

Figure 4A:
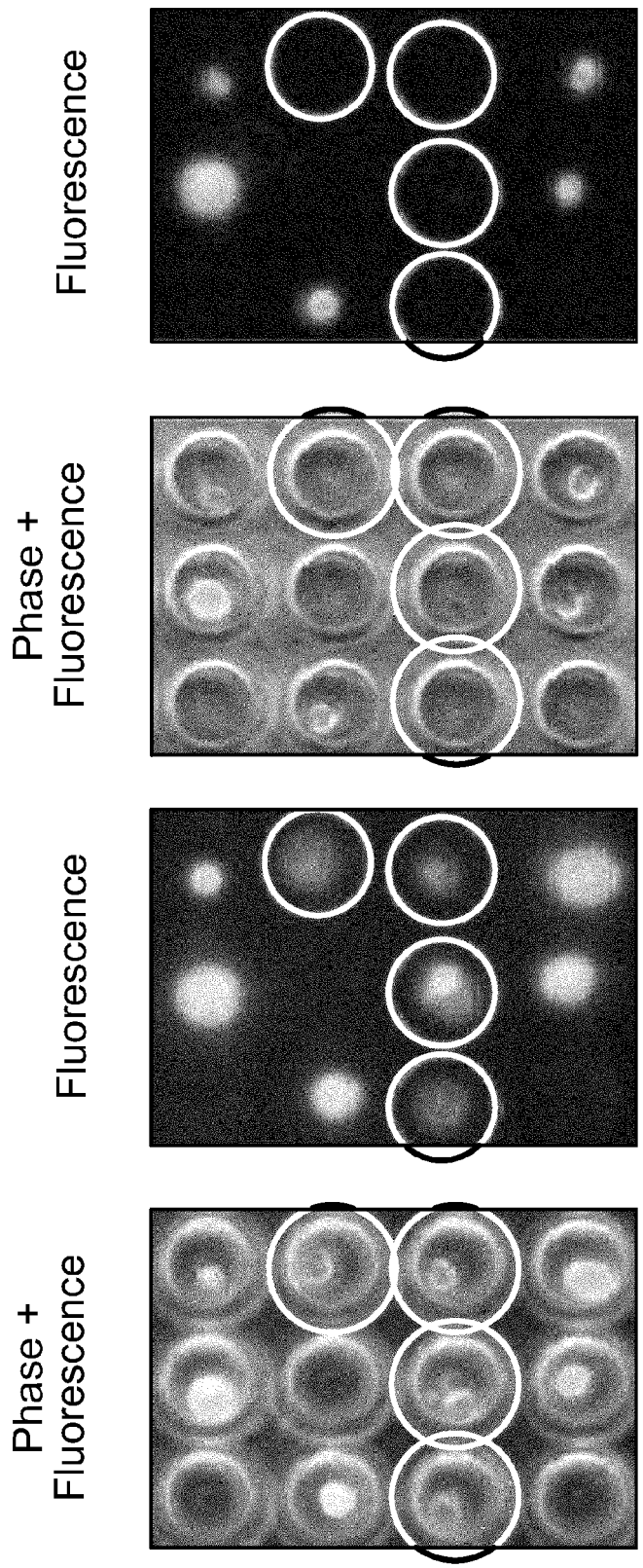
FIG. 4 demonstrates cell sorting using one embodiment of a device of this invention. A demonstrates random deposition of HL60 cells harboring either an orange or green label, applied to the device. B demonstrates the presence of only green cells in the array, following application of the optical force to remove orange labeled cells. (B) Sequence of images showing levitation and removal of a target cell. Illustrations qualitatively show cell state in each frame. 1—Cell at rest, 100 ms before laser is turned on. 2—Lateral optical gradient force moves cell to lateral center of beam. 3—Optical scattering force begins to levitate cell. 4—Scattering force levitates cell into flow field. 5—Fluid drag force overwhelms optical gradient force, releasing cell. (C) Tight localization of optical force. The ability to remove a single targeted cell residing in a doubly-loaded well is shown.

A microfluidic chamber as described in Example 1 was loaded with fluorescently tagged HL-60 cells. Orange- and green-labeled HL60 cells were randomly applied to the device, and the cells were imaged under phase contrast microscopy and fluorescence microscopy to determine respective placement of green versus orange cells in particular wells (FIG. 4A). Application of the laser to individual wells under flow conditions enabled the specific removal of orange-labeled cells.

Figure 4B:
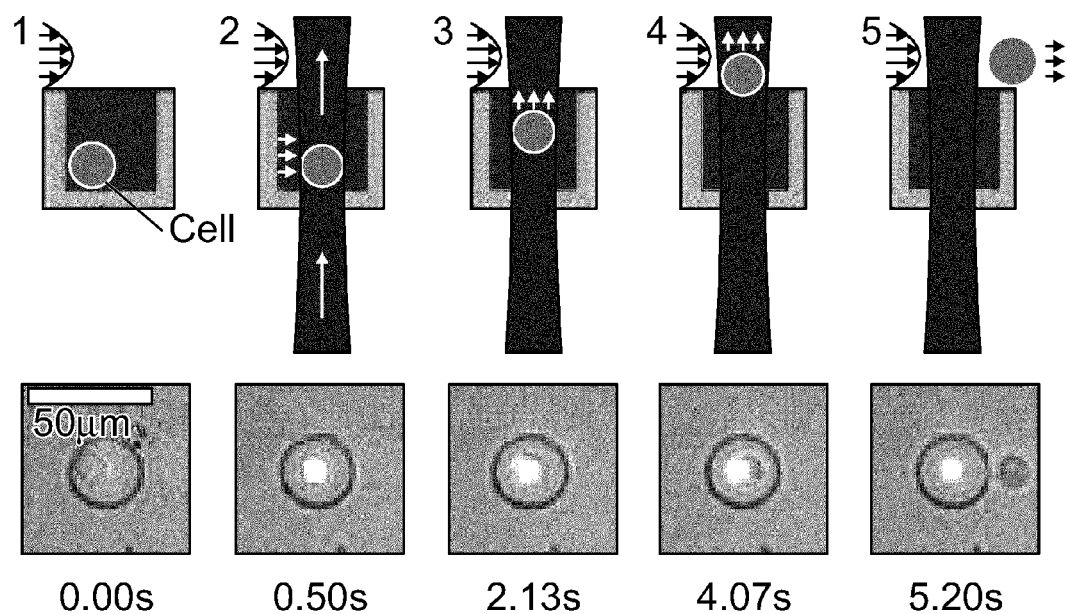
Figure 4C:
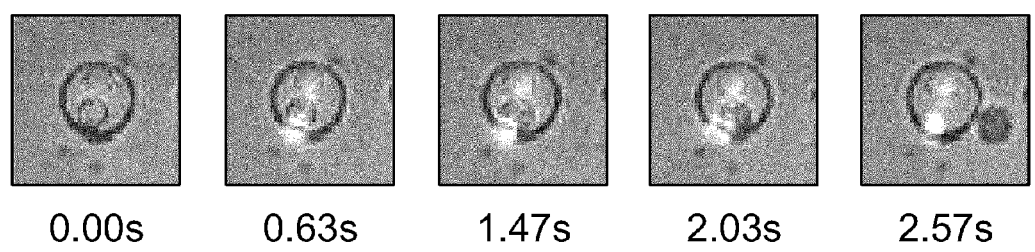

The actual process of cell removal has two qualitative phases: first, after the laser is focused onto the cell, the gradient force in the lateral beam dimension quickly drags the cell laterally into the beam center. Next, the scattering force overwhelms gravity and the small axial gradient force, and the cell is levitated up into the flow field. As the cell is levitated away from the laser focus, the local intensity and lateral gradient force drop due to beam divergence, and eventually Stokes drag from the fluid flow overcomes the lateral gradient force, releasing the cell into the flow stream (FIG. 4). A single cell can, in general, even be removed selectively from a well with multiple cells (FIGS. 4B-C), a testament to the tight localization of the optical force.

Figure 5:
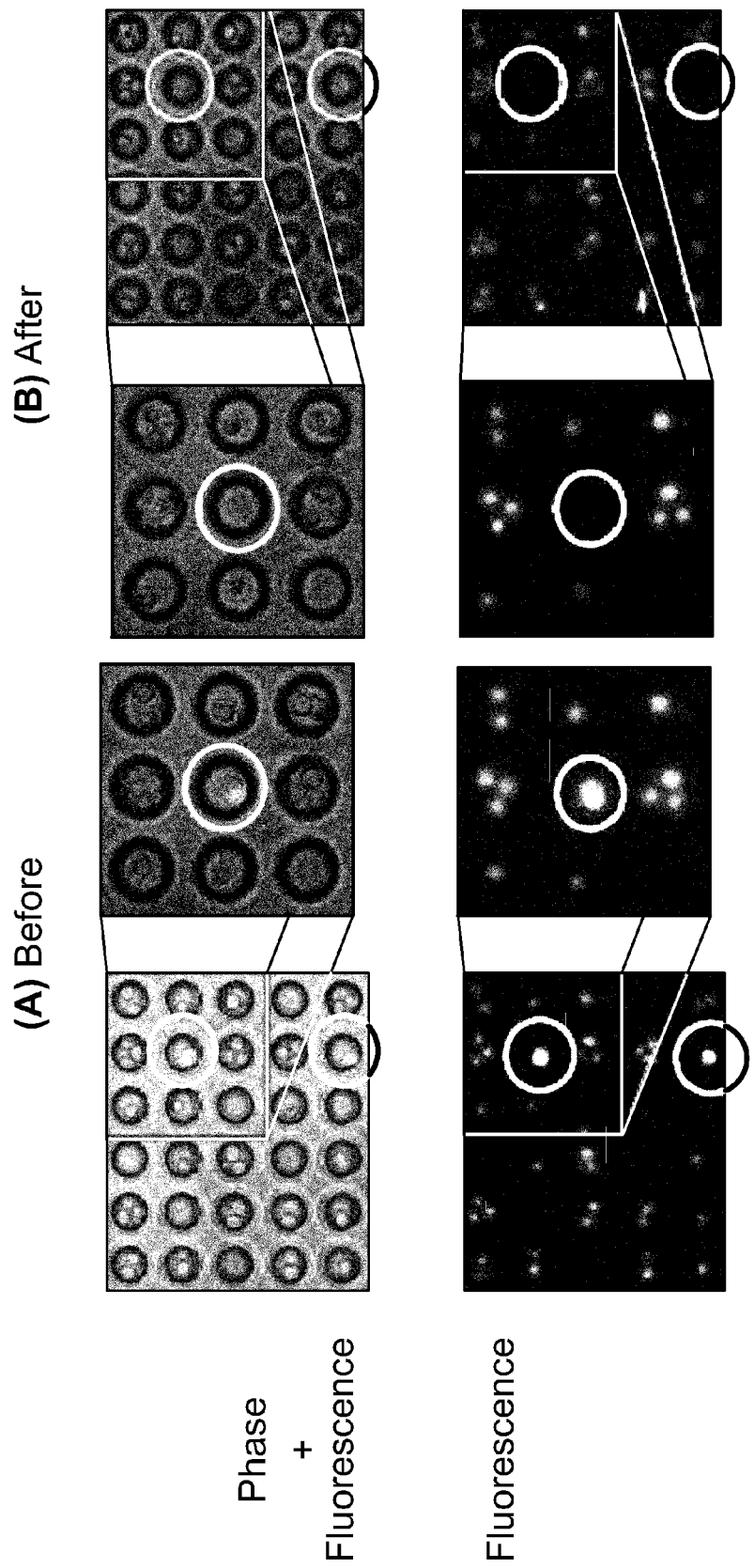
FIG. 5 demonstrates cell sorting using one embodiment of a device of this invention. In this embodiment, nuclear- and membrane-stained cells were mixed with cells comprising only nuclear staining. Using fluorescence microscopy, cells with membrane staining were identified (A) and removed (B), and image-based sorting of markers indicating intracellular localization of a target molecule was accomplished in this embodiment.

Another sort was conducted using nuclear-stained and membrane-stained cells (FIG. 5). Membrane stained cells were identified via fluorescence and phase contrast microscopy (yellow circles, in A panels) and sorted as above, from cells with exclusively nuclear staining. This demonstrates image-based sorting based upon localization, an assay that cannot be performed using flow cytometry.

While whole-cell fluorescence-based sorting has been conducted by other means known in the art, an image-based approach to whole-cell fluorescence-based sorting could allow sorting based on single-cell fluorescence levels monitored over time, which to date is not accomplished in a straightforward manner.

Figure 6:
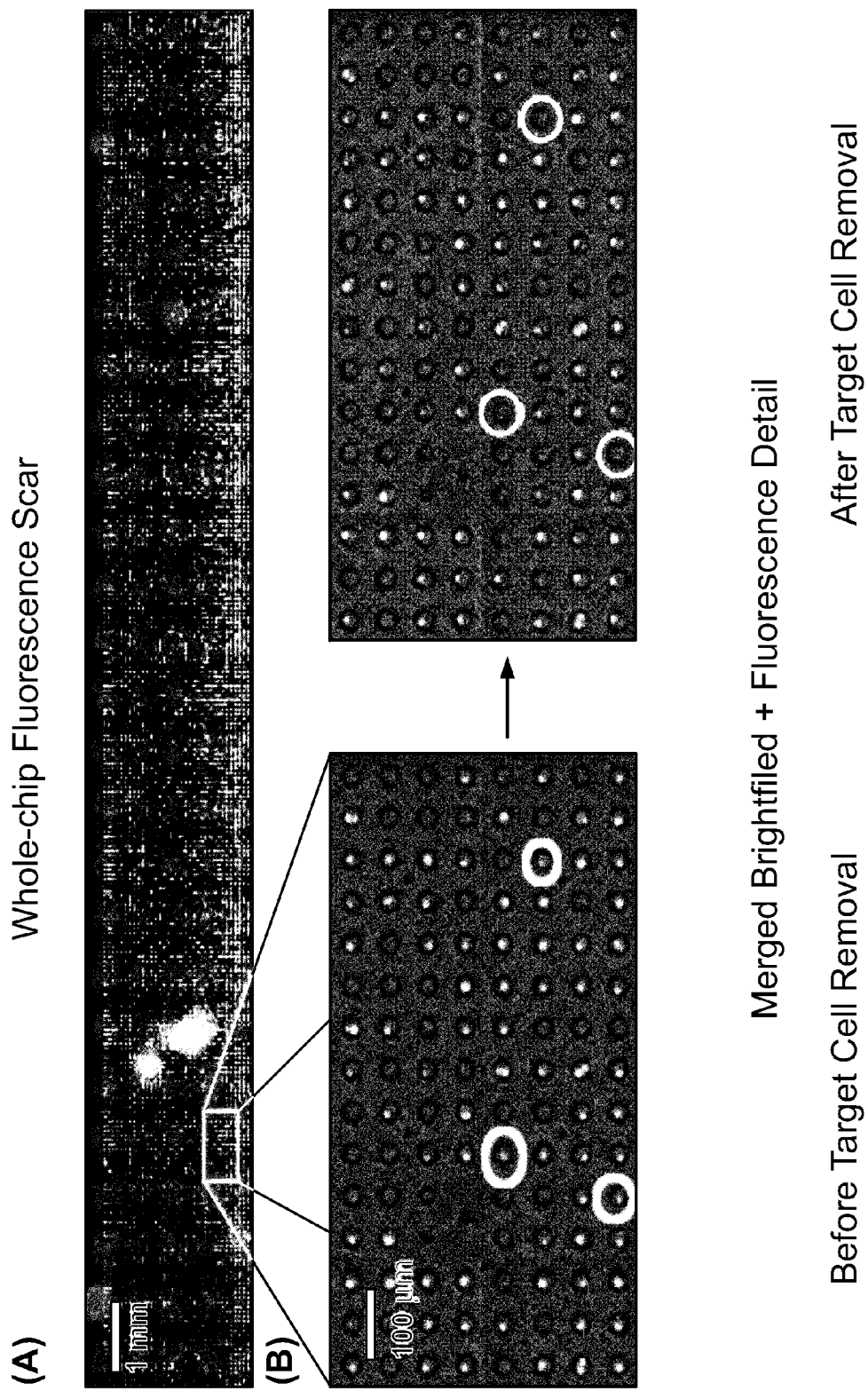
FIG. 6 demonstrates whole cell fluorescence-based cell sorting. A loaded 10,000-site array was scanned and orange-labeled cells were located. Selective release of orange cells (false-colored red) from their trap sites was accomplished, demonstrating the ability of image-based sorting based on time-resolved, whole cell fluorescence, a capability effectively missing from FACS. Chip-level detail, shown in (A), is intentionally oversaturated in order to make cell-containing sites more visible for viewing/printing.

To pursue this, it was desirable an image thousands of single cells and release single target cells from their trap sites based on whole-cell fluorescence. After loading the microwell array with a 50:1 ratio of CellTracker Green: CellTracker Orange-labeled cells, the entire array was scanned under brightfield and fluorescence illumination and the images were inspected to determine the location of orange-labeled cells. Array sites containing orange-labeled cells were noted, buffer flow was re-instated, and orange-labeled cells were selectively levitated into the flow field for removal (FIG. 6, circled cells). The process of releasing a cell, in some embodiments, takes about 18-45 seconds, with selecting and scanning to an array site, aligning the laser to the cell, and levitating and releasing a cell taking about 10 seconds, 5 seconds, and 3-30 seconds, respectively. Attempting removal of 60-70 cells per hour is feasible, which is an embodiment of this invention, for useful throughput in applications where 10's to ~100 rare cells are desired. The results obtained herein demonstrate that a more than 10,000-site array can be iteratively imaged using fluorescence to predicate single-cell sorting decisions.

FACS cannot resolve localization of a fluorophore within a cell. Such localization can be important when studying translocation events of proteins within cells or protein localization, among other applications. To demonstrate a sort predicated on fluorescence localization, a mixed population of MCF7 cells exhibiting nuclear fluorescence and MCF7 cells double-stained with CellTracker Orange and Green, which exhibited diffuse whole cell fluorescence was imaged and sorted (FIG. 6). The green double-stain served to demonstrate sorting verification. Selective removal of the nuclear-fluorescent cells was achieved, for this experiment despite the fact that the diffuse fluorescent signal was spectrally indistinguishable from the nuclear signal. A slightly higher power (150 mW) was utilized to image these cells as they were slightly larger in comparison to BA/F3 cells, although the short removal times for the two cells (6 s and 12 s) suggest that they could have also been removed with a typical exposure of 100 mW for ~20-30 s. Thus spatial and temporal fluorescence information can be obtained from multiple channels with any other image data, (i.e. brightfield images as shown in FIG. 6) to allow sorting of cells based on phenotypes far more complex than is practical or possible with FACS.

The beam was focused so that the beam waist was roughly equal to the cell diameter (~9 □m). In some embodiments, a choice is made not to use a larger beam waist in that in some circumstances it may waste power, e.g., with photons missing the cell. In some embodiments, a choice is made not to use a smaller beam waist, in order to avoid high local intensities and increase the axial gradient force, which in some embodiments, competes against the levitating scattering force.

In some embodiments, levitation and release of a cell from a well takes about 15-20 seconds, or in some embodiments, from about 3 to 30 seconds. In some embodiments, variations in cell size and shape affect the timing of levitation and release of a cell from a well.

In some embodiments, as the cell diameter approaches the well diameter, Stokes drag wall effects become more significant, leading to longer removal times for larger cells in the population.

In some embodiments, quickest removal is of significantly aspheric cells, such as those undergoing mitosis, as their asymmetry makes them easier to remove via the fluid flow after they are levitated slightly.

In some embodiments, removal efficiency may be determined, which in some embodiments represents the percentage of cells successfully removed from a well out of the total number of cells, for which removal was attempted. In some embodiments, such efficiency may vary between 25% and 100%, depending on the well dimensions used.

In some embodiments, as exemplified herein, 100% removal efficiency was achieved by using wells 30-µm in diameter and 35-µm in depth.

The methods/devices/apparatuses of this invention allow for straightforward image-based inspection and sorting of thousands of cells. The methods/devices/apparatuses of this invention allow for simple scalability to large sizes with minimal additional complexity. Sorting of cells from a functional 10,000 site array was shown feasible herein, and fabricating larger arrays is trivial.

A limitation of further scaling may be array inspection speed and image processing time to make sorting decisions, which in turn may be improved upon, depending upon the sorting decisions required and other parameters, as will be appreciated by one skilled in the art. In some embodiments data mining is readily accomplished, possibly constrained by similar considerations for any existing array-based method, inspection and data processing time, rather than by the specific technology used.

Array inspection time ultimately dictates the temporal resolution of assays. Exemplified herein is the visualization of a 10,000 site array under brightfield illumination and two fluorescence wavelengths in about 25 minutes when using a 10× objective lens. Faster image-based screening can be readily obtained in specific types of assays with minor modifications.

In temporal whole-cell fluorescence applications, where total cell fluorescence signal is the critical information to capture, simply placing a 0.5× de-magnifier before the CCD while using the same 10× objective lens could reduce this time by a factor of 4. Wells could likely be packed more densely; reducing the center-to-center distance between 30-µm-diameter wells from 65 □m to 45 □m would double the area density of trapped cells. With these two simple changes, we could achieve an eightfold increase in sampling rate for a given number of cells, yielding a 3-minute inspection time for a 10,000 site array. Using a larger CCD could further increase the rate.

Cell removal is currently simple and straightforward; software stores locations of target cells and scans the automated stage back to target sites for removal automatically. Automating fine laser alignment (which is now done manually) immediately before cell release would quicken release by ~5-7 s per site. Using slightly higher laser powers briefly to overcome surface interactions may also quicken cell release by a few seconds. The most dramatic improvements could be made by incorporating multiple beams, allowing quasi-parallel release. For instance, we could use a four-beam system with 125 mW beams and independently steer the beams via mirrors. This off-chip complexity is easily abstracted from the user, and provides a realistic avenue for scale up in release. These two changes could reduce the average total removal time per cell to ~10 s, making removal of 100-300 cells per hour practical, independent of the type of imaging assay employed. In addition, microwells need not be arranged in a grid-like fashion for large array-type experiments—microwell traps could be positioned throughout a substrate to enable addressable retrieval of particular cells in arbitrary alternative experiments. The technique generalizes easily to any application where the goal is to position cells in an environment, observe them using microscopy, and later retrieve particular cells.

The simplicity of the optical system depicted herein allowed for straightforward incorporation into widely used microscopes.

Example 3

Cell Viability in an Embodiment of an Opto-Fluidic Particle Sorter

Cell viability and potential for cell damage is a point of concern when using any cell manipulation technique. Use of a weakly focused 980-nm beam for up to 30 s at power levels of ~100 mW for cell manipulation is considerably gentler than parameters in many optical tweezers applications, where the beam is focused to micron-sized spots, sometimes at power levels up to ~1 W for longer durations. Considerable effort has been made to determine cell damage thresholds for optical manipulation. Studies have considered metrics including post-exposure clonability, motility, DNA damage, and viability, and the methods/devices/apparatuses for cell sorting can be compared utilizing existing methods versus those of this invention [Liang, H. et al. Biophys J 1996, 70, 1529-1533; Neuman, K. C. et al. Biophys J 1999, 77, 2856-2863; Liu, Y.; et al. J. Biophys J 1996, 71, 2158-2167; Mohanty, S. K. et al Radiation Research 2002, 157, 378-385; Wang, M. M. et al. Nature Biotechnology 2005, 23, 83-87]. Table 1 presents various parameters at onset of cell damage reported previously, and those obtained using an embodied device of this invention.

TABLE 1

| Ref. | Cell Type | λ (nm) | Power (W) | Exposure Time (s) | Spot Size (µm) | Power Density (W/cm$^2$) | Energy Density (J/cm$^2$) | Energy (J) | Damage |
|---|---|---|---|---|---|---|---|---|---|
| Liang[18] | CHO | 990 | 0.176 | 180 | 0.70 | 4.6e+7 | 8.2e+9 | 31.7 | yes |
| Liu[20] | Human Sperm | 1064 | 0.300 | 120 | 0.75 | 6.8e+7 | 8.1e+9 | 36.0 | yes |
| Mohanty[21] | NC37 Lymphoblast | 1064 | 0.120 | 30 | 0.75 | 2.7e+7 | 8.1e+8 | 3.6 | yes |

TABLE 1-continued

| Ref. | Cell Type | $\lambda$ (nm) | Power (W) | Exposure Time (s) | Spot Size ($\mu$m) | Power Density (W/cm$^2$) | Energy Density (J/cm$^2$) | Energy (J) | Damage |
|---|---|---|---|---|---|---|---|---|---|
| Wang[22] | HeLa | 1070 | 13.2 | 0.004 | 4.9 | 7.0e+7 | 2.8e+5 | 0.053 | No |
| Present | BA/F3 | 980 | 0.100 | 20 | 8.6 | 1.7e+5 | 3.4e+6 | 2.0 | No |

Table-1 is an adaptation of a supplemental table from Wang et al. with some reference to original literature to use more relevant data points for comparison with the present examples. The reported spot size is the spot diameter measured across the beam between points of 1/e$^2$ of maximum spot intensity as measured with an unsaturated CCD. Spot sizes listed for comparison are spot diameters calculated by d = 1.22☐(n × NA) according to the cited NA and wavelength in the reference. The operating point of Wang et al. was reported to induce no damage and is shown for comparison. The parameters utilized in these Examples are gentler than the damage threshold reported by Liang, Liu, and Mohanty, especially with respect to power density and energy density.

These health studies did not explicitly separate thermal damage-effects from strictly photon-damage effects. This is largely because, in general, heating due to optical tweezers is influenced heavily by absorption of the trapping medium, and typical temperature rises in water have been reported between ~1-10 K/100 mW optical power, with the lower end of the range reported for cell manipulation.

The large spot size used in the methods/devices/apparatuses of this invention result in power and energy densities orders of magnitude lower than reported damage thresholds. Further, three of the examples in Table-1 use wavelengths of ~1064 nm. Liang et al. showed that the 990-nm wavelength is considerably less harmful than 1064 nm, so damage thresholds from Liu and Mohanty may be more pessimistic than those possible at 980 nm. Therefore, the methods/devices/apparatuses of this invention provide for healthy, viable cell sorting

What is claimed is:

1. A particle sorting apparatus comprising:
   (a) a particle sorter, comprising:
      i. a substrate comprising two or more chambers, wherein said chambers are recessed into the substrate, and wherein said chambers are sized to accommodate a desired number of particles;
      ii. at least one inlet for the introduction of fluids comprising particles into said chambers, whereby one or more particles in said fluid are introduced into said sorter via said inlet to occupy said chambers;
      iii. at least one outlet for the collection of a fluid comprising particles from said chambers; and
      iv. a first region in fluid communication with an inlet valve and an outlet valve configured to accommodate a fluid flow between said inlet and outlet valves, wherein said region abuts and is in fluid communication with said chambers;
   (b) a detection system operationally connected to said sorter configured to detect desired particles for removal from said sorter; and
   (c) a controllable optical force source operationally connected to said sorter applying an optical force to said detected particles whose sorting is desired, wherein said optical force has a beam waist about comparable to a diameter of said detected particles, and wherein said optical force is configured to levitate said desired particle from the chamber it occupies to said fluid flow in said first region and thereby convey said desired particle to said outlet for removal from said sorter.

2. The particle sorting apparatus of claim 1, wherein said chambers are adhered to a surface of said substrate.

3. The particle sorting apparatus of claim 1, wherein said chambers are contiguous with said substrate.

4. The particle sorting apparatus of claim 1, wherein said substrate, said chambers, or a combination thereof are transparent or translucent.

5. The particle sorting apparatus of claim 1, wherein said substrate, said chambers, or a combination thereof comprise a material, which inhibits or abrogates particle adhesion.

6. The particle sorting apparatus of claim 1, wherein said substrate, said chambers, or a combination thereof comprise a material, which stimulates or enhances particle adhesion.

7. The particle sorting apparatus of claim 1, further comprising a controller to control fluid flow rate and pressure in said fluid flow in said first region through said sorter.

8. The particle sorting apparatus of claim 1, further comprising at least one environmental controller to regulate pH or temperature in said sorter.

9. The particle sorting apparatus of claim 1, wherein said sorter further comprises microchannels positioned proximally to said chambers, such that said optical force conveys said particles from said chambers to said microchannels.

10. The particle sorting apparatus of claim 9, wherein said microchannels are positioned proximally to said outlet, such that said particles are conveyed via said microchannels to said outlet.

11. The particle sorting apparatus of claim 1, wherein said substrate is a microchip.

12. The particle sorting apparatus of claim 1, wherein said apparatus further comprises a collection module operationally positioned proximally to said outlet, such that said particles are conveyed via said outlet to said collection module.

13. The particle sorting apparatus of claim 1, wherein said optical force source is a near infrared laser.

14. The particle sorting apparatus of claim 1, wherein said detection system is an optical detection system.

15. The particle sorting apparatus of claim 14, wherein said optical detection system comprises a microscope.

16. The particle sorting apparatus of claim 14, wherein said optical detection system comprises a light source and a detector.

17. The particle sorting apparatus of claim 16, wherein said detector detects scattered light.

18. The particle sorting apparatus of claim 16, wherein said detector detects fluorescence emissions.

19. The particle sorting apparatus of claim 1, further comprising channels linked to said outlet, such that sorted particles are conveyed from said sorter through said channels.

20. A method of particle sorting, said method comprising:
   (a) applying a fluid comprising particles to an inlet of a particle sorting apparatus, said apparatus comprising:
      (i) a particle sorter comprising:
         (A) a substrate comprising two or more chambers, wherein said chambers are sized to accommodate a desired number of particles;
         (B) at least one inlet for the introduction of fluids into said sorter;
         (C) at least one outlet for the collection of a fluid from said sorter; and (D) a first region in fluid communication with an inlet valve and an outlet valve configured to accommodate a fluid flow between said inlet and outlet valves, wherein said region abuts and is in fluid communication with said chambers;

(ii) a detection system operationally connected to said sorter; and (iii) a controllable optical force source operationally connected to said sorter applying an optical force to said detected particles whose sorting is desired, wherein said optical force has a beam waist about comparable to a diameter of said detected particles, and wherein said optical force is configured to levitate said desired particle from the chamber it occupies to said fluid flow in said first region and thereby convey said desired particle to said outlet for removal from said sorter;

b) detecting said particles and assigning at least a subset of said detected particles for removal; and c) applying said optical force under flow to said particles assigned for removal (i) whereby upon applying fluid to said device, said particles are accommodated in said chambers and application of said optical force to said subset of particles under flow conveys said subset of particles to said outlet.

21. The method of claim 20, wherein said particle sorter comprises chambers which are adhered to a surface of said substrate.

22. The method of claim 20, wherein said particle sorter comprises chambers which are contiguous with said substrate.

23. The method of claim 20, wherein said substrate, said chambers, or a combination thereof, of said particle sorter, are transparent or translucent.

24. The method of claim 20, wherein said substrate, said chambers, or a combination thereof, of said particle sorter, comprise a material, which inhibits or abrogates particle adhesion.

25. The method of claim 20, wherein said substrate, said chambers, or a combination thereof, of said particle sorter, comprise a material, which stimulates or promotes particle adhesion.

26. The method of claim 20, wherein said particles are cells.

27. The method of claim 26, wherein said particles are mammalian cells.

28. The method of claim 26, wherein said particles are bacteria.

29. The method of claim 20 or 26, wherein said particles comprise a detectable marker.

30. The method of claim 29, wherein said particles are sorted as a function of expression, presence, or localization of said detectable marker or a combination thereof.

31. The method of claim 29, wherein said detectable marker is a fluorescent molecule.

32. The method of claim 29, wherein said detectable marker is a an electron dense or light reflective molecule.

33. The method of claim 20, wherein said apparatus further comprises a controller for fluid flow rate and pressure through said sorter.

34. The method of claim 33, wherein said optical force is applied concurrent with or prior to the application of a relatively constant flow rate and pressure to said sorter.

35. The method of claim 20, wherein said apparatus further comprises at least one environmental controller to regulate pH or temperature in said sorter.

36. The method of claim 20, wherein said sorter further comprises microchannels positioned proximally to said chambers, such that said optical force conveys said particles from said chambers to said microchannels.

37. The method of claim 36, wherein said microchannels are positioned proximally to said outlet, such that said particles are conveyed via said microchannels to said outlet.

38. The method of claim 20, wherein said substrate in said sorter is a microchip.

39. The method of claim 20, wherein said apparatus further comprises a collection module operationally positioned proximally to said outlet, such that said particles are conveyed via said outlet to said collection module.

40. The method of claim 39, wherein said collection module comprises reagents for the assay of sorted particles.

41. The method of claim 40, wherein said collection module further comprises an apparatus for the detection and analysis of the results of said assay.

42. The method of claim 20, wherein said optical force source of said apparatus is a near infrared laser.

43. The method of claim 20, wherein said detection system of said apparatus is an optical detection system.

44. The method of claim 43, wherein said optical detection system comprises a microscope.

45. The method of claim 44, wherein said optical detection system comprises a light source and a detector.

46. The method of claim 45, wherein said detector detects scattered light.

47. The method of claim 45, wherein said detector detects fluorescence emissions.

48. The method of claim 20, whereby said detecting of said particles comprises assaying said particles.

49. The method of claim 48, whereby said assigning at least a subset of said detected particles for removal is a function of the results of said assaying.

50. The method of claim 20, whereby said detecting of said particles and said assigning at least a subset of said detected particles for removal is within a time frame of seconds to hours.

51. The method of claim 20, wherein said apparatus is a modular system.

52. The method of claim 50, wherein said sorter may be readily removed from or inserted into said apparatus.

53. The method of claim 20, whereby said detecting of said particles and said assigning at least a subset of said detected particles for removal is within a time frame of days to weeks.

54. The method of claim 53, whereby prior to said assigning, said sorter is removed from said apparatus and maintained under desired conditions which differ from that present in said apparatus.

55. The method of claim 20, wherein said apparatus further comprises channels linked to said outlet of said sorter, such that sorted particles are conveyed from said sorter through said channels.

56. The method of claim 55, wherein said apparatus comprises a second substrate comprising said sorter and said channels.

57. The method of claim 56, wherein particles are conveyed to desired regions on said second substrate via said channels.

58. The method of claim 56, wherein said second substrate is a microfluidic chip.

59. A method of particle patterning on a substrate, said method comprising:

(a) applying a fluid comprising particles to an inlet of a particle sorting apparatus, said apparatus comprising:

(i) a particle sorter comprising:
  (A) a first substrate comprising two or more chambers, wherein said chambers are sized to accommodate a desired number of particles;
  (B) at least one inlet for the introduction of fluids into said sorter;
  (C) at least one outlet for the conveyance of fluids out of said sorter;
  (D) a first region in fluid communication with an inlet valve and an outlet valve configured to accommodate a fluid flow between said inlet and outlet valves, wherein said region abuts and is in fluid communication with said chambers; and
  (E) a second substrate comprising said sorter and channels linked to said outlet of said sorter;
(ii) a detection system operationally connected to said sorter; and
(iii) an optical force source operationally connected to said sorter applying said optical force to said detected particles whose sorting is desired, wherein said optical force has a beam waist about comparable to a diameter of said detected particles, and wherein said optical force is configured to levitate said desired particle from the chamber it occupies to said fluid flow in said first region and thereby convey said desired particle to said outlet for removal from said sorter;
(b) detecting said particles and assigning at least a subset of said detected particles for conveyance from said sorter to at least a portion of said channels; and
(c) applying said optical force under flow to said particles assigned for conveyance;
  (i) whereby said optical force applied under flow conveys said particles to said channels and cessation of said optical force and said applied flow allows for patterning of said particles on said second substrate.

60. The method of claim 59, wherein said particle sorter comprises chambers which are adhered to a surface of said first substrate.

61. The method of claim 59, wherein said particle sorter comprises chambers which are contiguous with said first substrate.

62. The method of claim 59, wherein said first substrate, said second substrate, said chambers, or a combination thereof, are transparent or translucent.

63. The method of claim 59, wherein said first substrate, said second substrate, said chambers, said channels, or a combination thereof, comprise a material, which inhibits or abrogates particle adhesion.

64. The method of claim 59, wherein said first substrate, said second substrate, said chambers, said channels, or a combination thereof, comprise a material which promotes or enhances particle adhesion.

65. The method of claim 59, wherein said particles are cells.

66. The method of claim 65, wherein said particles are mammalian cells.

67. The method of claim 65, wherein said particles are bacteria.

68. The method of claim 59 or 65, wherein said particles comprise a detectable marker.

69. The method of claim 68, wherein said particles are sorted as a function of expression, presence, or localization, or a combination thereof of said detectable marker.

70. The method of claim 68, wherein said detectable marker is a fluorescent molecule.

71. The method of claim 68, wherein said detectable marker is an electron dense or light reflective molecule.

72. The method of claim 59, wherein said apparatus further comprises a controller for fluid flow rate and pressure through said sorter.

73. The method of claim 72, wherein said optical force is applied concurrent with or prior to the application of a relatively constant flow rate and pressure to said sorter.

74. The method of claim 59, wherein said apparatus further comprises at least one environmental controller to regulate pH or temperature in said sorter.

75. The method of claim 59, wherein said second substrate is a microchip.

76. The method of claim 59, wherein said apparatus further comprises inlets for the introduction of reagents for the assay of patterned particles.

77. The method of claim 76, wherein said apparatus further comprises a module for the detection and analysis of the results of said assay.

78. The method of claim 59, wherein said optical force source of said apparatus is a near infrared laser.

79. The method of claim 59, wherein said detection system of said apparatus is an optical detection system.

80. The method of claim 79, wherein said optical detection system comprises a microscope.

81. The method of claim 79, wherein said optical detection system comprises a light source and a detector.

82. The method of claim 81, wherein said detector detects scattered light.

83. The method of claim 81, wherein said detector detects fluorescence emissions.

84. The method of claim 59, whereby said detecting of said particles comprises assaying said particles.

85. The method of claim 83, whereby said assigning at least a subset of said detected particles for conveyance from said sorter is a function of the results of said assaying.

86. The method of claim 59, wherein said apparatus is a modular system.

* * * * *